(12) United States Patent
Rapaport et al.

(10) Patent No.: US 10,213,527 B2
(45) Date of Patent: *Feb. 26, 2019

(54) FUNCTIONALIZED TITANIUM BINDING PEPTIDES AND IMPLANTS COATED WITH SAME

(71) Applicant: Ben-Gurion University of the Negev Research and Development Authority, Beer-Sheva (IL)

(72) Inventors: Hanna Rapaport, LeHavim (IL); Anna Gittelman, Arad (IL)

(73) Assignee: Ben-Gurion University of the Negev Research and Development Authority, Beer-Sheva (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/667,655

(22) Filed: Aug. 3, 2017

(65) Prior Publication Data

US 2017/0328895 A1 Nov. 16, 2017

Related U.S. Application Data

(62) Division of application No. 14/405,192, filed as application No. PCT/IL2013/050476 on Jun. 3, 2013, now Pat. No. 9,731,048.

(60) Provisional application No. 61/654,883, filed on Jun. 3, 2012.

(51) Int. Cl.
| | |
|---|---|
| A61L 27/54 | (2006.01) |
| A61L 27/06 | (2006.01) |
| C07K 7/06 | (2006.01) |
| A61L 27/34 | (2006.01) |
| A61L 31/02 | (2006.01) |
| A61L 31/10 | (2006.01) |
| A61L 31/16 | (2006.01) |
| C07K 5/103 | (2006.01) |
| C07K 7/08 | (2006.01) |
| A61K 38/02 | (2006.01) |
| A61L 27/30 | (2006.01) |
| C01G 23/04 | (2006.01) |
| G01N 33/543 | (2006.01) |
| A61C 8/00 | (2006.01) |
| A61L 31/00 | (2006.01) |
| B82Y 30/00 | (2011.01) |

(52) U.S. Cl.
CPC .............. *A61L 27/54* (2013.01); *A61K 38/02* (2013.01); *A61L 27/06* (2013.01); *A61L 27/30* (2013.01); *A61L 27/34* (2013.01); *A61L 31/022* (2013.01); *A61L 31/10* (2013.01); *A61L 31/16* (2013.01); *C01G 23/043* (2013.01); *C07K 5/1013* (2013.01); *C07K 7/06* (2013.01); *C07K 7/08* (2013.01); *G01N 33/54393* (2013.01); *A61C 8/0012* (2013.01); *A61L 31/00* (2013.01); *A61L 2300/25* (2013.01); *A61L 2300/252* (2013.01); *A61L 2300/412* (2013.01); *A61L 2300/606* (2013.01); *A61L 2430/12* (2013.01); *A61L 2430/24* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 9,731,048 B2* | 8/2017 | Rapaport | ............... A61L 27/54 |
| 2005/0020809 A1 | 1/2005 | Gazit | |
| 2006/0234947 A1 | 10/2006 | Gazit | |
| 2010/0015197 A1 | 1/2010 | Rapaport | |
| 2013/0225512 A1 | 8/2013 | Gazit et al. | |
| 2015/0119334 A1* | 4/2015 | Rapaport | ............... A61L 27/06 |
| | | | 514/16.7 |

FOREIGN PATENT DOCUMENTS

| | | |
|---|---|---|
| EP | 1589088 | 10/2005 |
| EP | 1661910 | 5/2006 |
| EP | 1814976 | 8/2007 |
| WO | WO 2006/055531 | 5/2006 |
| WO | WO 2013/183048 | 12/2013 |
| WO | WO2013183048 | * 12/2013 |

OTHER PUBLICATIONS

Communication Pursuant to Article 94(3) EPC dated Dec. 9, 2016 From the European Patent Office Re. Application No. 13737423.7. (7 Pages).
Communication Pursuant to Article 94(3) EPC dated Jan. 28, 2016 From the European Patent Office Re. Application No. 13737423.7.
International Preliminary Report on Patentability dated Dec. 18, 2014 From the International Bureau of WIPO Re. Application No. PCT/IL2013/050476.
International Search Report and the Written Opinion dated Aug. 22, 2013 From the International Searching Authority Re. Application No. PCT/IL2013/050476.
Invitation Pursuant to Article 94(3) and Rule 71(1) EPC dated Jun. 8, 2017 From the European Patent Office Re. Application No. 13737423.7. (4 pages).

(Continued)

*Primary Examiner* — Maury A Audet

(57) ABSTRACT

An isolated peptide is disclosed. The peptide comprises a titanium oxide binding amino acid sequence connected to a heterologous biologically active amino acid sequence via a beta sheet breaker linker, wherein:
  (i) the titanium oxide binding amino acid sequence is selected to bind coordinatively with titanium oxide;
  (ii) the titanium oxide binding amino acid sequence is selected to induce a beta sheet structure; and
  (ii) the titanium oxide binding amino acid sequence binds to titanium oxide with a higher affinity than said biologically active amino acid sequence binds to the titanium oxide under physiological conditions.

Use of the peptides and titanium devices comprising same are also disclosed.

15 Claims, 17 Drawing Sheets
(16 of 17 Drawing Sheet(s) Filed in Color)
Specification includes a Sequence Listing.

(56) References Cited

OTHER PUBLICATIONS

Office Action dated Dec. 15, 2015 From the Israel Patent Office Re. Application No. 236053 and Its Translation Into English.
Office Action dated Feb. 28, 2017 From the Israel Patent Office Re. Application No. 236053 and Its Translation Into English. (4 Pages).
Official Action dated Oct. 31, 2016 From the US Patent and Trademark Office Re. U.S. Appl. No. 14/405,192.
Restriction Official Action dated Jun. 3, 2016 From the US Patent and Trademark Office Re. U.S. Appl. No. 14/405,192.
Baneyx et al. "Selection and Analysis of Solid-Binding Peptides", Current Opinion in Biotechnology, XP022244964, 18(4): 312-317, Sep. 14, 2007. p. 315, col. 1, Para 2.
Gertler et al. "Characterizing the Adsorption of Peptides to TiO2 in Aqueous Solutions by Liquid Chromatography", Langmuir, XP002711087, 26(9): 6457-6463, May 4, 2010. p. 6462, cols. 1-2, p. 6463.
Meyers et al. "Endothelialization of Titanium Surfaces", Advanced Materials, XP002528796, 19(18): 2492-2498, Aug. 2, 2007. p. 2492, col. 2, Para 2, p. 2493, col. 1, Para 2—col. 2, Para 2, Table 1, p. 2495, col. 2, Para 3—p. 2496, col. 1, Para 1.
Raffaini et al. "Molecular Modelling of Protein Adsorption on the Surface of Titanium Dioxide Polymorphs", Philosophical Transactions, Series A, Mathematical, Physical, and Engineering Sciences, XP002711088, 370(1963): 1444-1462, Mar. 28, 2012. p. 1450, Para 1, Fig. 1, p. 1451, Fig. 2, p. 1454, Para 2, p. 1456-1458.
Sano et al. "A Hexapeptide Motif That Electrostatically Binds to the Surface of Titanium", Journal of the American Chemical Society, JACS, XP002904281, 125(47): 14234-14235, Nov. 26, 2003. p. 14234, col. 1, Para 5, p. 14235, col. 1, Para 1, p. 14235, col. 2, Para 2.
Zreiqat et al. "Differentiation of Human Bone-Derived Cells Grown on GRGDSP-Peptide Bound Titanium Surfaces", Journal of Biomedical Materials Research, XP002358271, 64A(1): 105-113, Jan. 1, 2003. p. 106, col. 1, Para 3—col. 2, Para 1, Table 1, p. 110, col. 1, Para 2—p. 111, col. 1, Para 1, p. 112, col. 1, Para 1.

\* cited by examiner

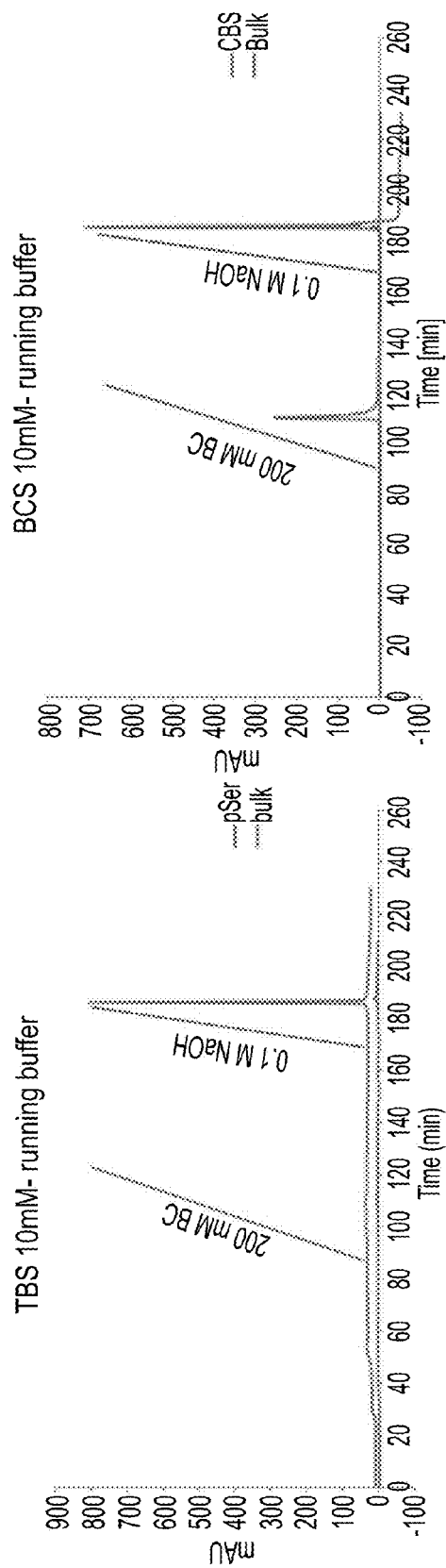

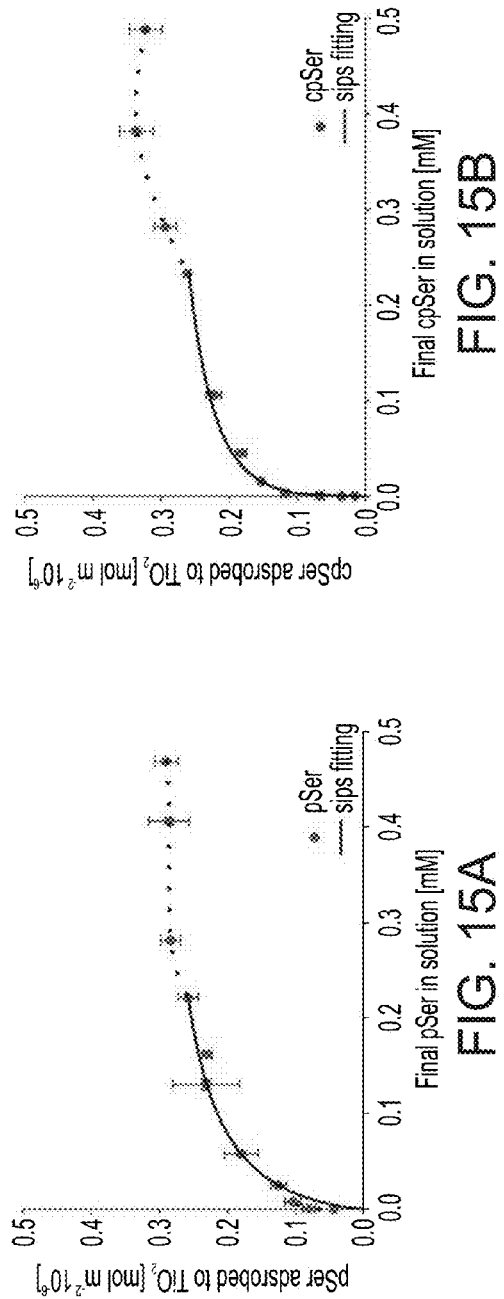
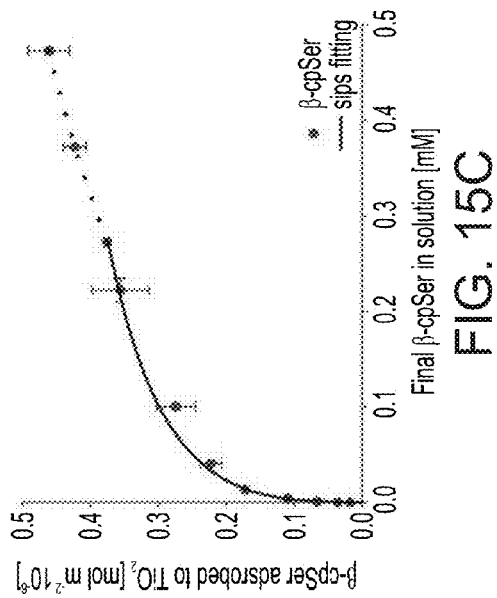
FIG. 15A
FIG. 15B
FIG. 15C

SEQUENCE LISTING

```
<160> NUMBER OF SEQ ID NOS: 27

<210> SEQ ID NO 1
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 1

Pro Ser Trp Ser Trp Gly Gly Gly Glu Glu Glu Glu Glu
1               5                   10

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue
<220> FEATURE:
<221> NAME/KEY: misc_feature
<222> LOCATION: (3)..(3)
<223> OTHER INFORMATION: Phosphorylated residue

<400> SEQUENCE: 2

Ser Trp Ser Trp
1
```

```
<210> SEQ ID NO 3
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue
<220> FEATURE:
<221> NAME/KEY: misc_feature
<222> LOCATION: (3)..(3)
<223> OTHER INFORMATION: Phosphorylated residue

<400> SEQUENCE: 3

Ser Phe Ser
1

<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 4

Pro Ser Phe Ser Gly Gly Glu Glu Glu
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: L-DOPA
<220> FEATURE:
<221> NAME/KEY: misc_feature
<222> LOCATION: (2)..(2)
<223> OTHER INFORMATION: X is a hydrophobic amino acid
<220> FEATURE:
<221> NAME/KEY: misc_feature
<222> LOCATION: (3)..(3)
<223> OTHER INFORMATION: L-DOPA
<220> FEATURE:
<221> NAME/KEY: misc_feature
<222> LOCATION: (4)..(4)
<223> OTHER INFORMATION: X is a hydrophobic amino acid

<400> SEQUENCE: 5

Xaa Xaa Xaa Xaa
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (1)..(1)
<223> OTHER INFORMATION: Phosphorylated residue
<220> FEATURE:
<221> NAME/KEY: misc_feature
<222> LOCATION: (2)..(2)
<223> OTHER INFORMATION: Xaa is any hydrophobic amino acid
<220> FEATURE:
<221> NAME/KEY: misc_feature
<222> LOCATION: (3)..(3)
<223> OTHER INFORMATION: Phosphorylated residue
<220> FEATURE:
<221> NAME/KEY: misc_feature
<222> LOCATION: (4)..(4)
<223> OTHER INFORMATION: Xaa is any hydrophobic amino acid

<400> SEQUENCE: 6

Ser Xaa Ser Xaa
1

<210> SEQ ID NO 7
<211> LENGTH: 5
<212> TYPE: PRT
<213> ORGANISM: Artificial sequence
<220> FEATURE:
<223> OTHER INFORMATION: Synthetic peptide

<400> SEQUENCE: 7

Glu Glu Glu Glu Glu
1               5

<210> SEQ ID NO 8
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue
<220> FEATURE:
<221> NAME/KEY: misc_feature
<222> LOCATION: (3)..(3)
<223> OTHER INFORMATION: Phosphorylated residue

<400> SEQUENCE: 8

Ser Phe Ser Trp
1

<210> SEQ ID NO 9
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: L-DOPA or phosphoserine
<220> FEATURE:
<221> NAME/KEY: misc_feature
<222> LOCATION: (2)..(2)
<223> OTHER INFORMATION: Can be any hydrophobic amino acid
<220> FEATURE:
<221> NAME/KEY: misc_feature
<222> LOCATION: (3)..(3)
<223> OTHER INFORMATION: L-DOPA or phosphoserine
<220> FEATURE:
<221> NAME/KEY: misc_feature
<222> LOCATION: (4)..(4)
<223> OTHER INFORMATION: Can be any hydrophobic amino acid
```

```
<220> FEATURE:
<221> NAME/KEY: misc_feature
<222> LOCATION: (8)..(12)
<223> OTHER INFORMATION: Can be aspartic acid or glutamic acid

<400> SEQUENCE: 9

Xaa Xaa Xaa Xaa Gly Gly Gly Xaa Xaa Xaa Xaa Xaa
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 10

Pro Ser Phe Ser Gly Gly Glu Glu Glu Glu Glu
1               5                   10

<210> SEQ ID NO 11
<211> LENGTH: 5
<212> TYPE: PRT
<213> ORGANISM: Artificial sequence
<220> FEATURE:
<223> OTHER INFORMATION: Synthetic peptide

<400> SEQUENCE: 11

Asp Asp Asp Asp Asp
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 12

Pro Ser Phe Ser Trp Gly Gly Gly Glu Glu Glu Glu Glu
1               5                   10

<210> SEQ ID NO 13
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
```

```
<223> OTHER INFORMATION: Phosphorylated residue

<400> SEQUENCE: 13

Pro Ser Phe Ser Trp Gly Gly Gly
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Phosphorylated residue

<400> SEQUENCE: 14

Pro Ser Ser Phe Trp Gly Gly Gly
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue

<400> SEQUENCE: 15

Ser Phe Gly Gly Gly Glu Glu Glu
1               5

<210> SEQ ID NO 16
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue

<400> SEQUENCE: 16

Ser Phe Gly Gly Gly Glu Glu Glu Glu Glu
1               5                   10

<210> SEQ ID NO 17
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue

<400> SEQUENCE: 17

Ser Phe Glu Glu Glu
1               5

<210> SEQ ID NO 18
<211> LENGTH: 7
<212> TYPE: PRT
```

```
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue

<400> SEQUENCE: 18

Ser Phe Glu Glu Glu Glu
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Phosphorylated residue

<400> SEQUENCE: 19

Ser Phe Gly Gly Gly
1               5

<210> SEQ ID NO 20
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(18)
<223> OTHER INFORMATION: Can be missing
<220> FEATURE:
<221> NAME/KEY: misc_feature
<222> LOCATION: (7)..(18)
<223> OTHER INFORMATION: Can be missing
<220> FEATURE:
<221> NAME/KEY: misc_feature
<222> LOCATION: (11)..(18)
<223> OTHER INFORMATION: Can be missing
<220> FEATURE:
<221> NAME/KEY: misc_feature
<222> LOCATION: (13)..(18)
<223> OTHER INFORMATION: Can be missing

<400> SEQUENCE: 20

Pro Asp Phe Asp Phe Asp Phe Asp Phe Asp Phe Asp Phe Asp Phe Asp
1               5                   10                  15

Phe Asp

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Phosphorylated residue

<400> SEQUENCE: 21

Ser Ser Phe Trp
1
```

```
<210> SEQ ID NO 22
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 22

Pro Ser Trp Ser Trp
1               5

<210> SEQ ID NO 23
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 23

Pro Ser Phe Ser
1

<210> SEQ ID NO 24
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: L-DOPA
<220> FEATURE:
<221> NAME/KEY: misc_feature
<222> LOCATION: (3)..(3)
<223> OTHER INFORMATION: Can be any hydrophobic amino acid
<220> FEATURE:
<221> NAME/KEY: misc_feature
<222> LOCATION: (4)..(4)
<223> OTHER INFORMATION: L-DOPA
<220> FEATURE:
<221> NAME/KEY: misc_feature
<222> LOCATION: (5)..(5)
<223> OTHER INFORMATION: Can be any hydrophobic amino acid

<400> SEQUENCE: 24

Pro Xaa Xaa Xaa Xaa
1               5

<210> SEQ ID NO 25
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
```

```
<222> LOCATION: (2)..(2)
<223> OTHER INFORMATION: Phosphorylated residue
<220> FEATURE:
<221> NAME/KEY: misc_feature
<222> LOCATION: (3)..(3)
<223> OTHER INFORMATION: Can be any hydrophobic amino acid
<220> FEATURE:
<221> NAME/KEY: misc_feature
<222> LOCATION: (4)..(4)
<223> OTHER INFORMATION: Phosphorylated residue
<220> FEATURE:
<221> NAME/KEY: misc_feature
<222> LOCATION: (5)..(5)
<223> OTHER INFORMATION: Can be any hydrophobic amino acid

<400> SEQUENCE: 25

Pro Ser Xaa Ser Xaa
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Phosphorylated residue
<220> FEATURE:
<221> NAME/KEY: misc_feature
<222> LOCATION: (4)..(4)
<223> OTHER INFORMATION: Phosphorylated residue

<400> SEQUENCE: 26

Pro Ser Phe Ser Trp
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Can be phosphoserine or L-dopa
<220> FEATURE:
<221> NAME/KEY: misc_feature
<222> LOCATION: (3)..(3)
<223> OTHER INFORMATION: Can be any hydrophobic amino acid
<220> FEATURE:
<221> NAME/KEY: misc_feature
<222> LOCATION: (4)..(4)
<223> OTHER INFORMATION: Can be phosphoserine or L-dopa
<220> FEATURE:
<221> NAME/KEY: misc_feature
<222> LOCATION: (5)..(5)
<223> OTHER INFORMATION: Can be any hydrophobic amino acid

<400> SEQUENCE: 27

Pro Xaa Xaa Xaa Xaa
1               5
```

FUNCTIONALIZED TITANIUM BINDING PEPTIDES AND IMPLANTS COATED WITH SAME

RELATED APPLICATIONS

This application is division of U.S. patent application Ser. No. 14/405,192 Filed on Dec. 3, 2014 which is a National Phase of PCT Patent Application No. PCT/IL2013/050476 having International Filing Date of Jun. 3, 2013, which claims the benefit of priority under 35 USC § 119(e) of U.S. Provisional Patent Application No. 61/654,883 filed on Jun. 3, 2012. The contents of the above applications are all incorporated by reference as if fully set forth herein in their entirety.

SEQUENCE LISTING STATEMENT

The ASCII file, entitled 70539SequenceListing.txt, created on Aug. 3, 2017, comprising 9,743 bytes, submitted concurrently with the filing of this application is incorporated herein by reference.

FIELD AND BACKGROUND OF THE INVENTION

The present invention, in some embodiments thereof, relates to functionalized titanium binding peptides and, more particularly, but not exclusively, to titanium binding peptides which are capable of promoting bone growth and mineralization.

Attempts to use titanium for implant fabrication dates to the late 1930's. It was found that titanium was tolerated in cat femurs, as was stainless steel and vitalium (a CoCrMo alloy). Titanium's lightness and good mechanical and chemical properties are salient features for implant applications. One titanium alloy (Ti6Al4V) is widely used to manufacture implants. The main alloying elements of this alloy are aluminium (5.5-6.5%) and vanadium (3.5-4.5%). Whilst the strength of the titanium alloys varies from lower than to equal to that of stainless steel, when compared by specific strength (strength per density), the titanium alloys outperform any other implant material.

More than 1000 tonnes (2.2 million pounds) of titanium devices of every description and function are implanted in patients worldwide every year, including for bone and joint replacement, dental implants, maxillo and cranio/facial treatments and cardiovascular devices. Light, strong and totally bio-compatible, titanium is one of few materials that naturally match the requirements for implantation in the human body.

The natural selection of titanium for implantation is determined by a combination of most favourable characteristics including immunity to corrosion, bio-compatibility, strength, low modulus and density and the capacity for joining with bone and other tissue—osseointegration. The mechanical and physical properties of titanium alloys combine to provide implants which are highly damage tolerant. The human anatomy naturally limits the shape and allowable volume of implants. The lower modulus of titanium alloys compared to steel is a positive factor in reducing bone resorbtion. Two further parameters define the usefulness of the implantable alloy, the notch sensitivity,—the ratio of tensile strength in the notched vs. un-notched condition, and the resistance to crack propagation, or fracture toughness. Titanium scores well in both cases. Typical NS/TS ratios for titanium and its alloys are 1.4-1.7 (1.1 is a minimum for an acceptable implant material). Fracture toughness of all high strength implantable alloys is above 50 MPam-1/2 with critical crack lengths well above the minimum for detection by standard methods of non-destructive testing.

Titanium (Ti) spontaneously forms an oxide layer up to a thickness of about 2 to 5 nm both in air and in the body, providing corrosion resistance. However, the normal oxide layer of titanium is not sufficiently bioactive to form a direct bond with juxtaposed bone, which may translate into a lack of osseointegration, leading to long-term failure of titanium implants.

In the past, many attempts have been made to improve the surface properties of Ti-based implants; e.g., by modifying Ti topography, chemistry, and surface energy, in order to better integrate into bone. Surface modification techniques include mechanical methods such as sand blasting, chemical methods such as acid etching, and the use of various coatings. A disadvantage of these approaches is that neither the mechanical nor the chemical methods produce highly controllable topological properties, and cell/tissue adherence may be unpredictable or insufficient for practical use. In some cases, the methods may cause formation of surface residuals, which can be interfere with osteoblast (bone forming cell) adherence and function.

Despite progress in modifying metal surfaces to improve tissue and cell adhesion properties, adequate in vivo osseointegration on implant prostheses remains a challenge. Substrates that promote significant bone-tissue interactions with biomaterial surfaces over a period of time would be highly desirable. In order to ensure effective tissue adhesion, and thus clinical success of orthopaedic/dental implants, it is important to develop stable, biocompatible surfaces that enhance osteoblast functions for new bone formation. Additionally, the increasing importance of antimicrobial and other bioactive agents for in vivo implants requires improved materials and more effective means of releasing drugs at selected sites in the body.

Gertler et al [Langmuir, 2010) teach titanium surfaces attached to peptides.

U.S. Patent Application No. 20100015197 teaches amphiphilic peptides and peptide matrices thereof useful in vitro and in situ biomineralization and inducing bone repair.

Meyers et al [Advanced Materials, 2007, 19, 2492-2498] teaches a 20-30 mer peptide that comprises a titanium binding domain and a domain that binds to endothelial cells. The peptides were identified using a genetically engineered peptide library. The drawback of this approach lies in the panning procedure which uses limited adsorption and desorption conditions. The panning enriches the electrostatically physiosorbed peptides, while leaving strongly bound ones unrevealed.

SUMMARY OF THE INVENTION

According to an aspect of some embodiments of the present invention there is provided an isolated peptide comprising a titanium oxide binding amino acid sequence connected to a heterologous biologically active amino acid sequence via a beta sheet breaker linker, wherein:

(i) the titanium oxide binding amino acid sequence is selected to bind coordinatively with titanium oxide;

(ii) the titanium oxide binding amino acid sequence is selected to induce a beta sheet structure; and (ii) the titanium oxide binding amino acid sequence binds to titanium oxide with a higher affinity than the biologically active amino acid sequence binds to the titanium oxide under physiological conditions.

According to an aspect of some embodiments of the present invention there is provided an isolated polynucleotide encoding the isolated peptides described herein.

According to an aspect of some embodiments of the present invention there is provided an article of manufacture comprising a titanium surface and the isolated peptide described herein adsorbed to the surface.

According to an aspect of some embodiments of the present invention there is provided a method of generating or repairing a tissue, the method comprising implanting the article of manufacture described herein into a subject in need thereof, thereby generating or repairing the tissue.

According to some embodiments of the invention, the isolated peptide comprises naturally occurring amino acids.

According to some embodiments of the invention, the isolated peptide comprises at least one synthetic amino acid.

According to some embodiments of the invention, the isolated peptide comprises at least one D amino acid.

According to some embodiments of the invention, the titanium oxide binding amino acid sequence binds to titanium oxide with at least 2 fold higher affinity than the biologically active amino acid sequence.

According to some embodiments of the invention, the beta sheet breaker linker comprises naturally occurring amino acids.

According to some embodiments of the invention, the beta sheet breaker linker comprises synthetic amino acids.

According to some embodiments of the invention, the beta sheet breaker amino linker comprises 2-7 repeating glycine residues.

According to some embodiments of the invention, the beta sheet breaker amino acid linker is set forth by Gly-Gly-Gly.

According to some embodiments of the invention, the beta sheet breaker amino linker is a chemical linker.

According to some embodiments of the invention, the titanium oxide binding amino acid sequence comprises no more than 7 carboxyl amino acid residues.

According to some embodiments of the invention, the titanium oxide binding amino acid sequence comprises alternating hydrophilic, negatively charged amino acids and hydrophobic amino acids.

According to some embodiments of the invention, the alternating hydrophilic and hydrophobic amino acid sequence is not repeated more than 7 times.

According to some embodiments of the invention, at least one of the amino acids of the titanium oxide binding amino acid sequence is phosphorylated.

According to some embodiments of the invention, the titanium oxide binding amino acid sequence comprises the sequence Y-X-Y-X, wherein X is any hydrophobic amino acid and Y is selected from the group consisting of glutamic acid, aspartic acid, phosphoserine and L-DOPA.

According to some embodiments of the invention, the titanium oxide binding amino acid sequence comprises the sequence Y-X-Y, wherein X is any hydrophobic amino acid and Y is selected from the group consisting of glutamic acid, aspartic acid, phosphoserine and L-DOPA.

According to some embodiments of the invention, the titanium oxide binding amino acid sequence comprises the sequence Y-Y-X-X, wherein X is any hydrophobic amino acid and Y is selected from the group consisting of glutamic acid, aspartic acid, phosphoserine and L-DOPA.

According to some embodiments of the invention, the X is selected from the group consisting of valine, phenylalanine, leucine, isoleucine and tryptophan.

According to some embodiments of the invention, the Y is pSer.

According to some embodiments of the invention, the titanium oxide binding amino acid sequence comprises the sequence pSer-X-pSer-X (SEQ ID NO: 6), wherein X is any hydrophobic amino acid.

According to some embodiments of the invention, the titanium oxide binding amino acid sequence comprises the sequence as set forth in SEQ ID NO: 8 or SEQ ID NO: 2.

According to some embodiments of the invention, the C terminus of the titanium oxide binding amino acid sequence is attached to an N terminus of the biologically active amino acid sequence via the linker.

According to some embodiments of the invention, the N terminus of the titanium oxide binding amino acid sequence is attached to a C terminus of the biologically active amino acid sequence via the linker.

According to some embodiments of the invention, the biologically active amino acid sequence is selected from the group consisting of an osteoinductive or osteoconductive amino acid sequence, a mineralizing amino acid sequence, an anti-inflammatory amino acid sequence, a cell binding amino acid sequence, a cell migration amino acid sequence and an anti-bacterial amino acid sequence.

According to some embodiments of the invention, the osteoinductive or osteoconductive amino acid sequence comprises acidic amino acids.

According to some embodiments of the invention, the osteoinductive or osteoconductive amino acid sequence comprises at least 1 glutamic acid residue or aspartic acid residue.

According to some embodiments of the invention, the osteoinductive or osteoconductive amino acid sequence comprises 3-15 repeating glutamic acid residues or aspartic acid residues.

According to some embodiments of the invention, the sequence of the osteoinductive or osteoconductive amino acid sequence is set forth in SEQ ID NO: 7.

According to some embodiments of the invention, the osteoinductive or osteoconductive amino acid sequence is selected from the group consisting of a BMP amino acid sequence, an FGF amino acid sequence, a TGF amino acid sequence, an EGF amino acid sequence and a fibrinogen amino acid sequence.

According to some embodiments of the invention, the biologically active amino acid sequence is no longer than 50 amino acids.

According to some embodiments of the invention, the peptide is no longer than 50 amino acids.

According to some embodiments of the invention, the sequence as set forth in Z-X-Z-X-(Gly)$_3$-(Y)$_5$ (SEQ ID NO: 9) where Z is L-dopa or phosphoserine, where X is any hydrophobic amino acid and Y is aspartic acid or glutamic acid.

According to some embodiments of the invention, the isolated peptide comprises the sequence as set forth in SEQ ID NO: 1 or SEQ ID NO: 12.

According to some embodiments of the invention, the isolated peptide comprises the sequence as set forth in SEQ ID NO: 3, 4 or 10.

According to some embodiments of the invention, the isolated peptide comprises the sequence as set forth in SEQ ID NO: 14 or 21.

According to some embodiments of the invention, the titanium oxide binding amino acid sequence comprises the sequence as set forth by Pro-pSer-X-pSer-X (SEQ ID NO:

6), where X is a hydrophobic amino acid, the biologically active amino acid sequence is set forth by SEQ ID NO: 7.

According to some embodiments of the invention, the titanium oxide binding amino acid sequence comprises a sequence selected from the group consisting of SEQ ID NO: 2, SEQ ID NO: 3 and SEQ ID NO: 21.

According to some embodiments of the invention, when the titanium oxide binding amino acid sequence comprises the sequence as set forth by L-DOPA-X-L-DOPA-X (SEQ ID NO: 5), where X is a hydrophobic amino acid, the biologically active amino acid sequence is set forth by SEQ ID NO: 7.

According to some embodiments of the invention, the titanium oxide binding amino acid sequence comprises the sequence PSer-Phe.

According to some embodiments of the invention, the peptide comprises the sequence selected from the group consisting of SEQ ID NO: 15, SEQ ID NO: 16, SEQ ID NO: 17, SEQ ID NO: 18 and SEQ ID NO: 19.

According to some embodiments of the invention, the article of manufacture is an implant.

According to some embodiments of the invention, the article of manufacture is a dental implant.

According to some embodiments of the invention, the implant is selected from the group consisting of a hip prosthesis, a knee prosthesis, a heart valve and an intravascular stent.

According to some embodiments of the invention, the tissue is selected from the group consisting of bone, cartilage and cardiac tissue.

According to some embodiments of the invention, the article of manufacture is for treating a disorder selected from the group consisting of a bone disorder, a cartilage disorder, a cardiac disorder and a dental disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A depicts the functional amino acid in the peptide.

FIG. 1B illustrates how the combination between the peptide and titanium implant will promote calcium-Phosphate mineralization and improve implant-bone integration.

FIG. 2 is a schematic illustration of how a peptide of embodiments of the invention binds to the titanium surface.

FIG. 3 is a schematic illustration of how the binding was analyzed by chromatography.

Figure 4:
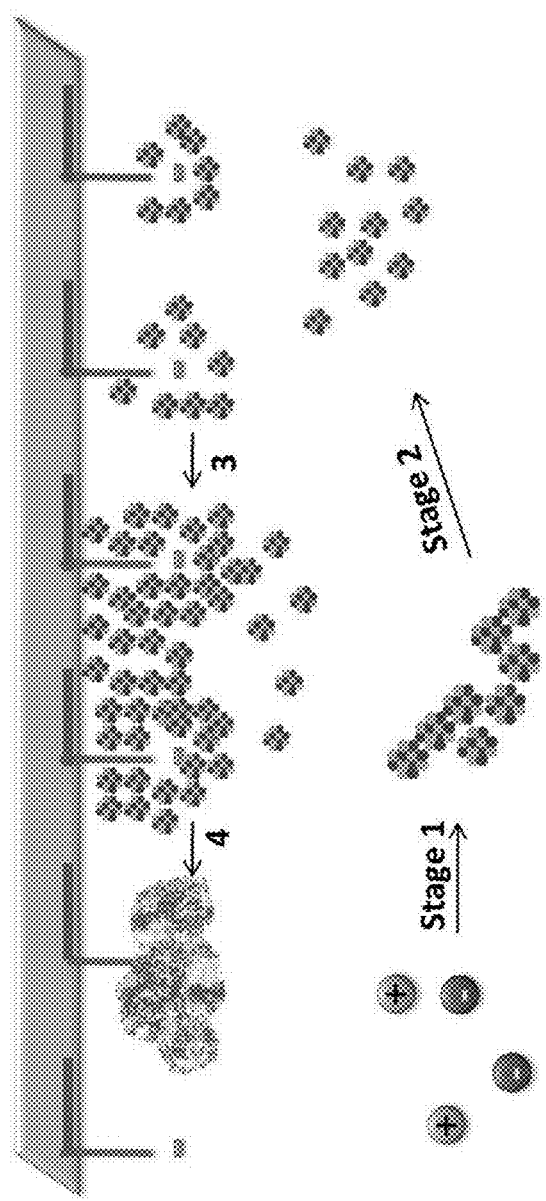

FIG. 4 is a schematic illustration of surface-directed mineralization of calcium phosphate. In stage 1, aggregates of calcium-phosphate appear. The clusters approach a surface with chemical functionality. In stage 2, pre-nucleation clusters aggregate near the surface, with loose aggregates still in solution. In stage 3, further aggregation causes densification near the surface. In stage 4, nucleation of amorphous spherical particles occurs at the surface only.

Figure 5:
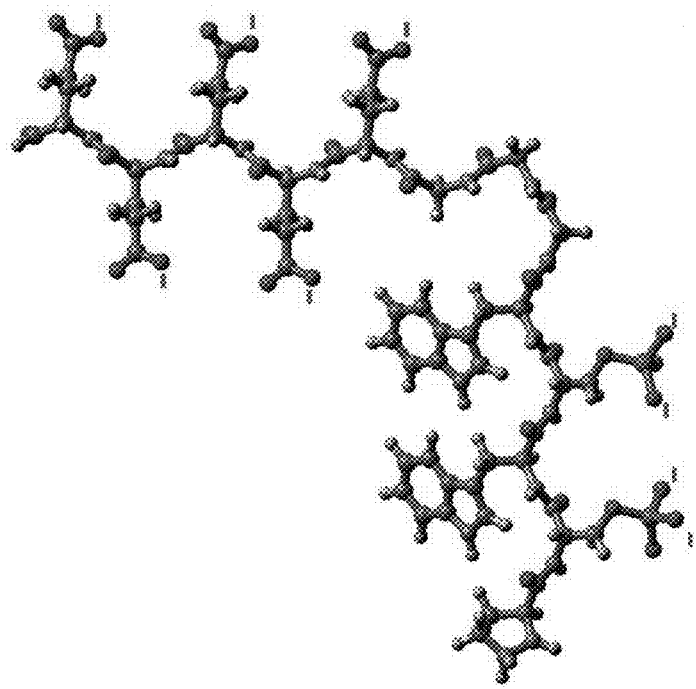

FIG. 5 is a schematic representation of one of the peptides of the present invention (SEQ ID NO: 1).

Figure 6:
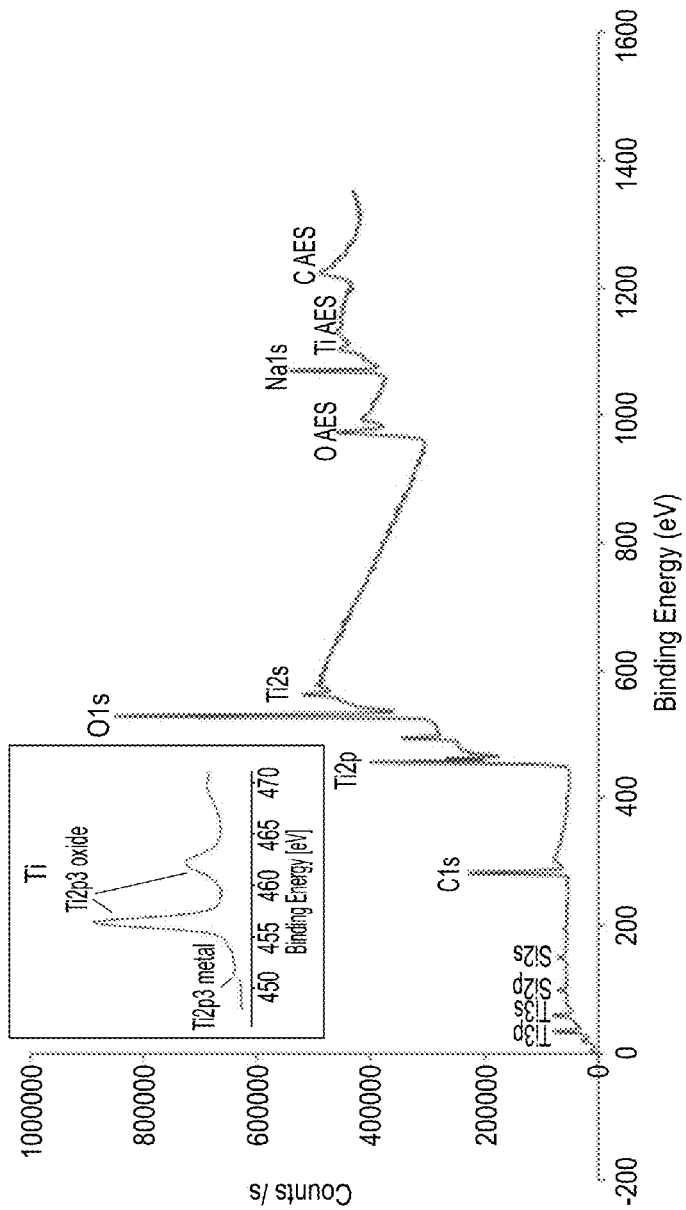

FIG. 6 is XPS spectra of Ti slides following 8 hours on a heating plate.

FIGS. 7A-7B are chromatograms of PpSer on $TiO_2$ anatase column. Adsorption of 0.4 mg/ml PpSer (SEQ ID NO: 1) in 10 mM TBS pH 7.4 (A) and 0.8 mg/ml PpSer (SEQ ID NO: 1) in CBS 10 mM pH 7.5 (B), followed by pH 7.4 (0-200 mM) sodium bicarbonate elution gradient, followed by NaOH (0-0.1M) elution gradient.

Figures 8A, 8B:
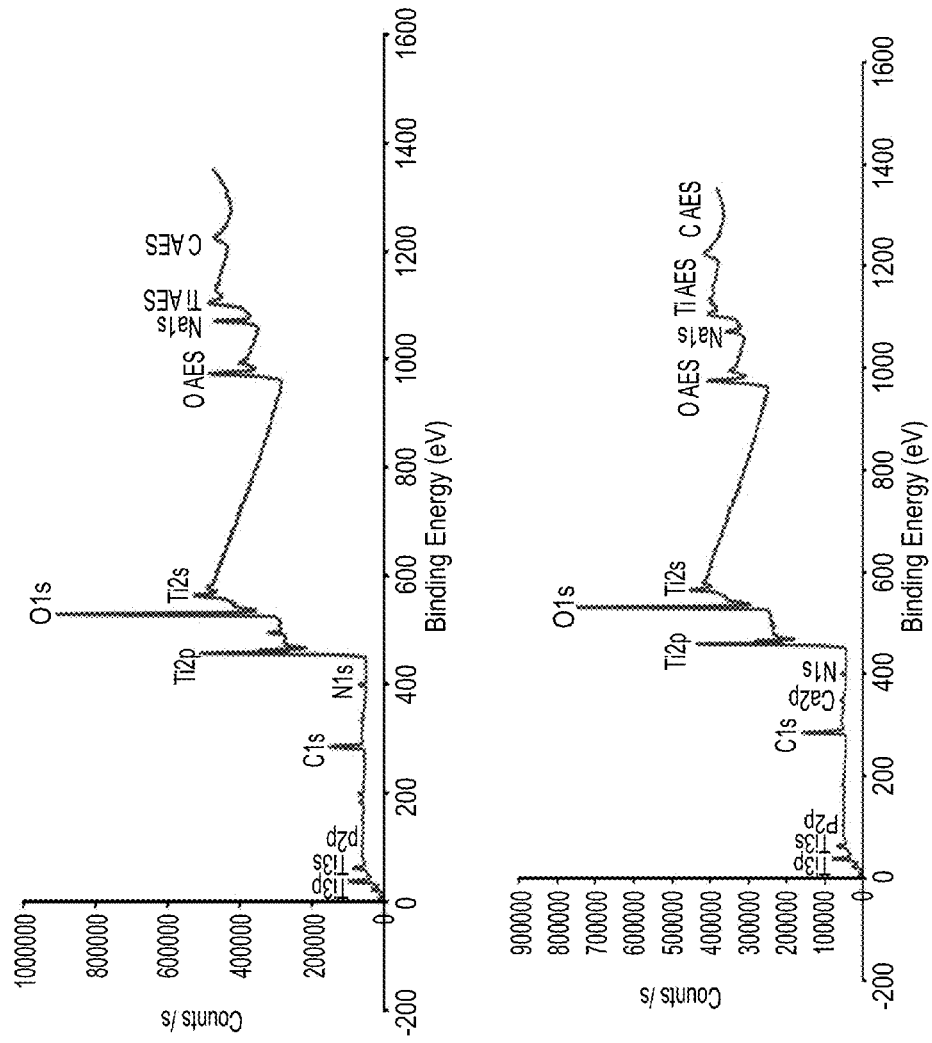

FIGS. 8A-8B are XPS spectra of peptide (SEQ ID NO: 1) diluted in TBS 10 mM to 0.2 mg/ml and bonded to $TiO_2$ (8A) and XPS spectra of surface b after 40 min in SBF (8B).

Figure 9:
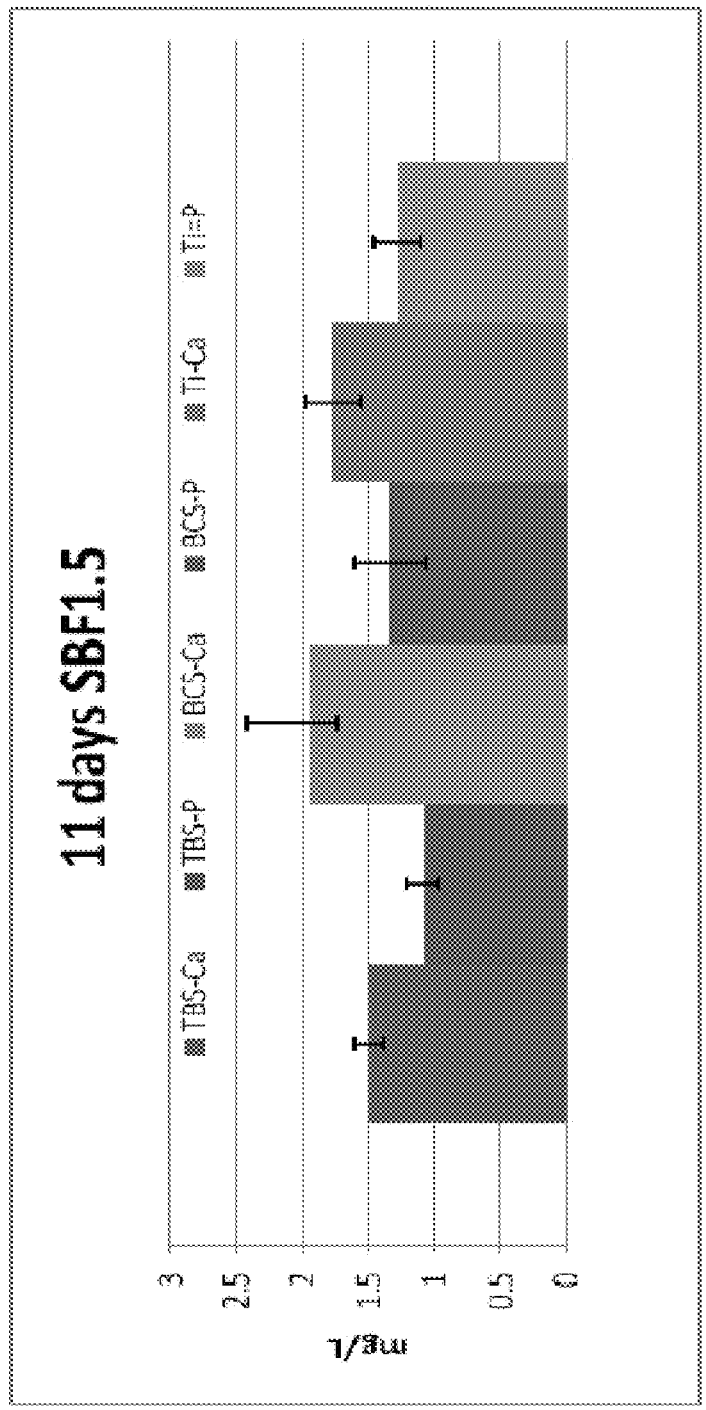

FIG. 9. Calcium and phosphate ion concentration detected in peptide coated samples that were soaked in SBF for 11 days. The samples were withdrawn from SBF after 11 days and immediately washed with ethanol to remove residual solution. The dried samples were then soaked in 0.1 M HCl to dissolve all the mineral and samples of the acidic solution were measured by ICP for calcium, phosphate and potassium ions (the latter were in negligible concentrations). The figure shows that the samples coated with peptide in presence of BCS exhibited the highest mineralization. Noteworthy, in these experiments the titanium oxide surface itself induces mineralization too. This result is in accordance with the expected anionic charges on the titanium surface. In addition, phosphate ions from the solution may coordinatively bind to the titanium and induce mineralization. Nevertheless, the peptide coating is expected to improve the binding strength between the mineralized layer and the titanium substrate.

Figures 10A, 10B:
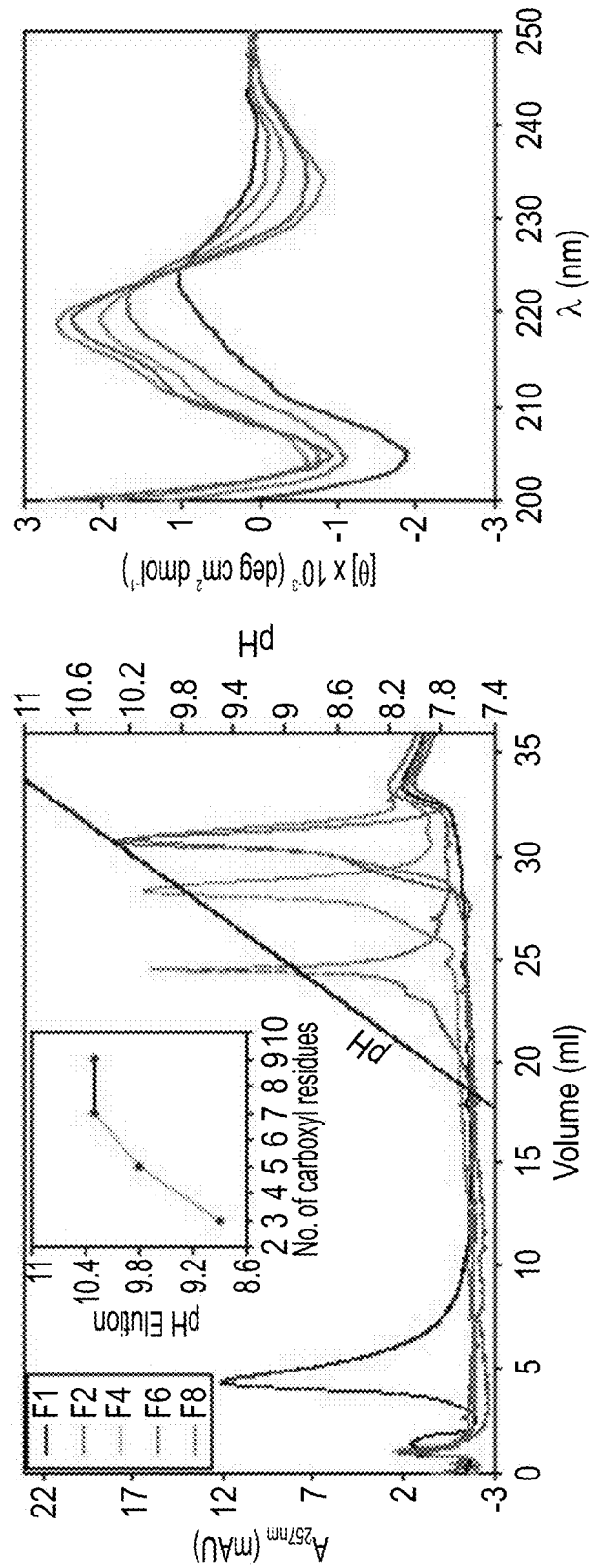

FIGS. 10A-10B (A) Chromatograms of PF1, PF2, PF4, PF6 and PF8 on TiO2 anatase column. Adsorption in 10 mM TBS pH 7.4, followed by pH (7.4-11) elution gradient. The gradient profile represents pH at the end of the column. Inset show the effect of carboxylic groups number on adsorption. (B) CD spectra in the adsorption medium, at 20° C.

Figure 11B:
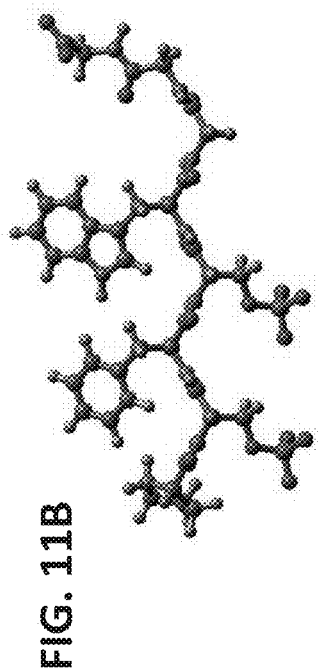
Figure 11C:
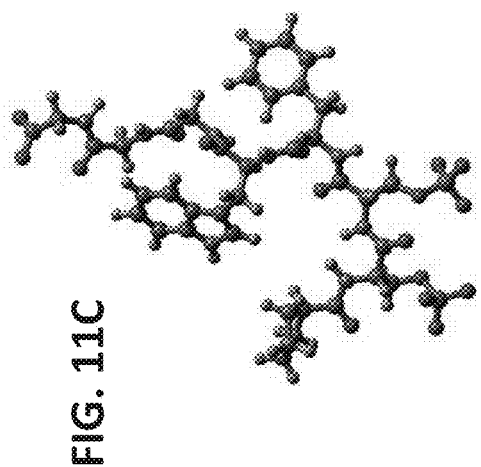
Figure 11A:
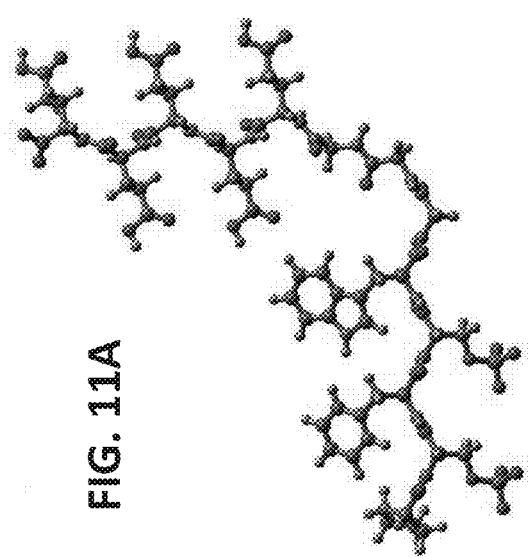

FIGS. 11A-11C are schematic illustrations of 'pSer' peptide—SEQ ID NO: 12 (A) and the control peptides 'cpSer'—SEQ ID NO: 13 (B) and β-cpSer—SEQ ID NO: 14 (C).

Figure 12:
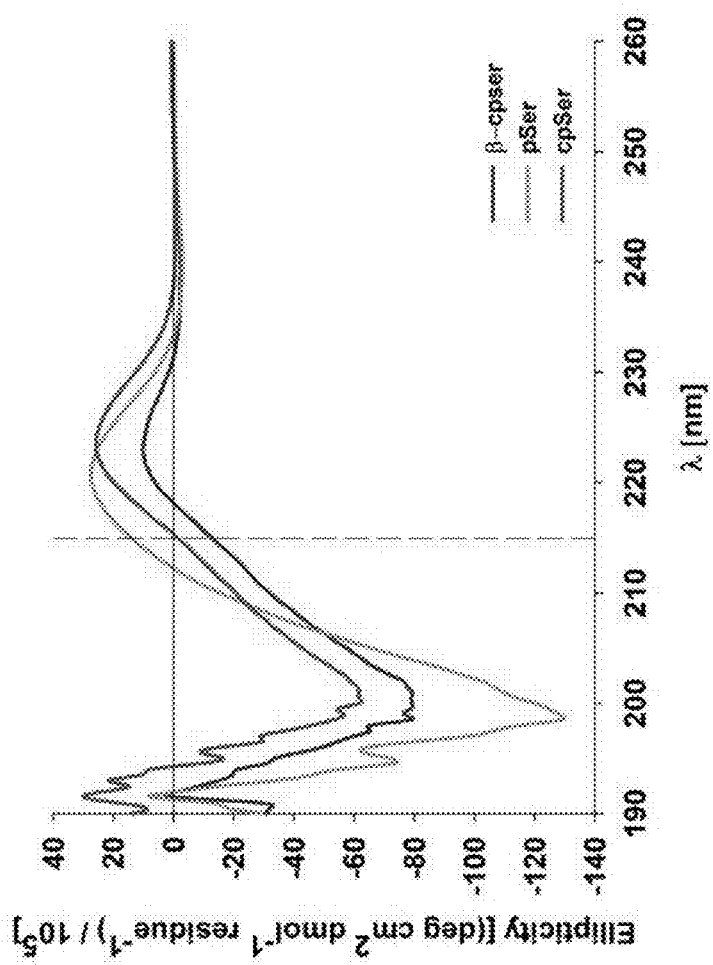

FIG. 12. CD spectra of pSer, cpSer and β-cpSer peptides. Each of the peptides was dissolved in 10 mM TBS (pH7.4) solution to a final concentration of 0.4 mg/ml. The same result was observed for a final peptide concentration of 0.2 mg/ml.

Figure 13:
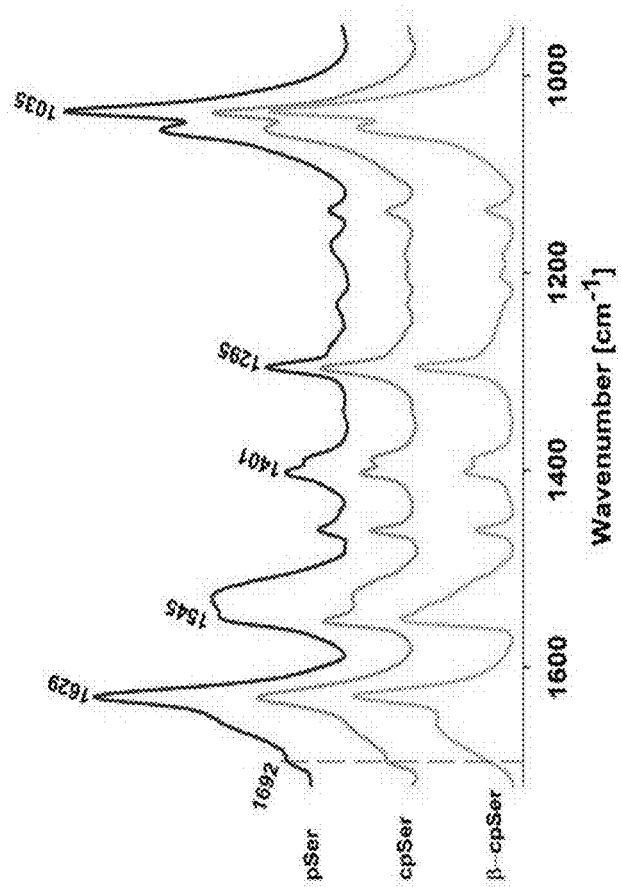

FIG. 13. Attenuated total reflection spectra of pSer, cpSer and β-cpSer peptides dissolved in 10 mM TBS (pH=7.4) and dried on ZnSe prism.

Figures 14A, 14B:
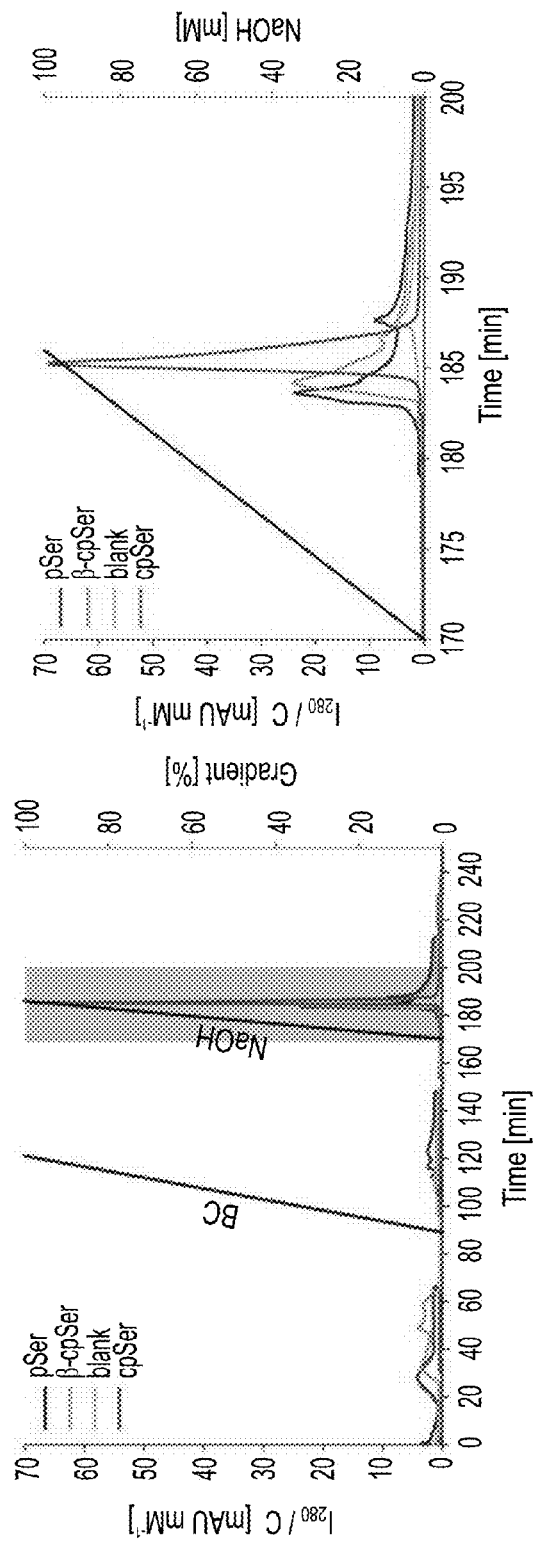

FIGS. 14A-14B. Chromatograms of pSer, cpSer and β-cpSer peptides on $TiO_2$ anatase column. The chromatograms presented as peptide adsorption at 280 nm normalized to peptide concentration. Adsorption was performed in 10 mM TBS pH 7.4 followed by sodium bicarbonate (0-200 mM) and NaOH (0-0.1 M) elution gradients. Marked area expanded at the right showing the peptides elution peaks.

FIGS. 15A-15C. Adsorption isotherm plots of pSer, cpSer and β-cpSer peptides onto $TiO_2$ particles, in 10 mM TBS pH=7.4. Continuous line represents the Sips adsorption fitting.

Figure 16:
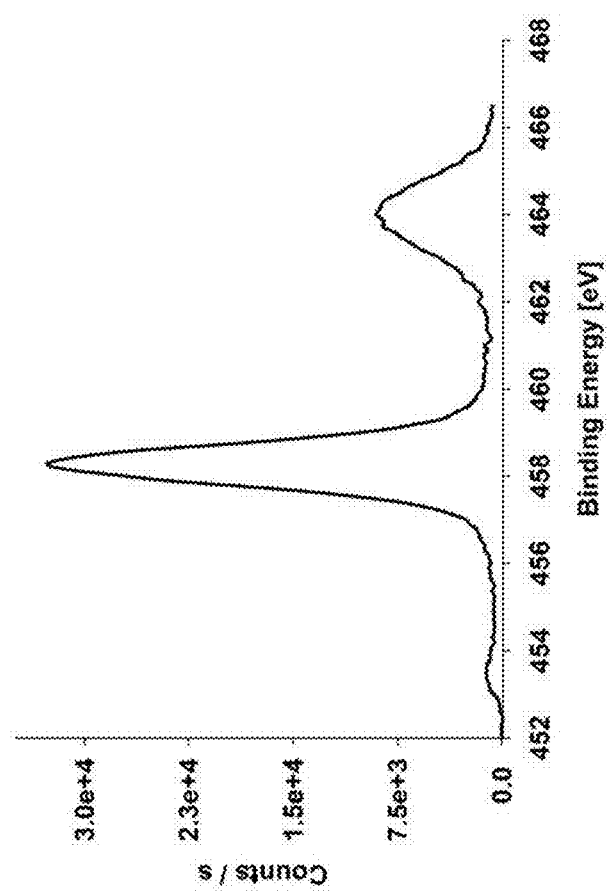

FIG. 16. XPS measurements of $TiO_2$ surface.

Figure 17B:
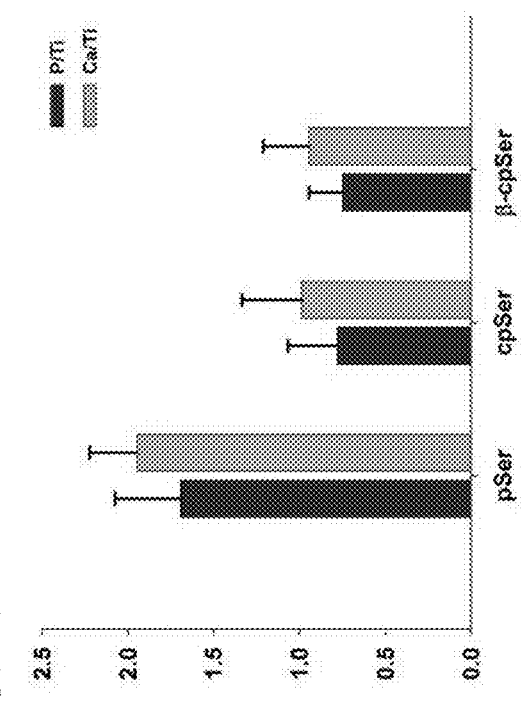
Figure 17A:
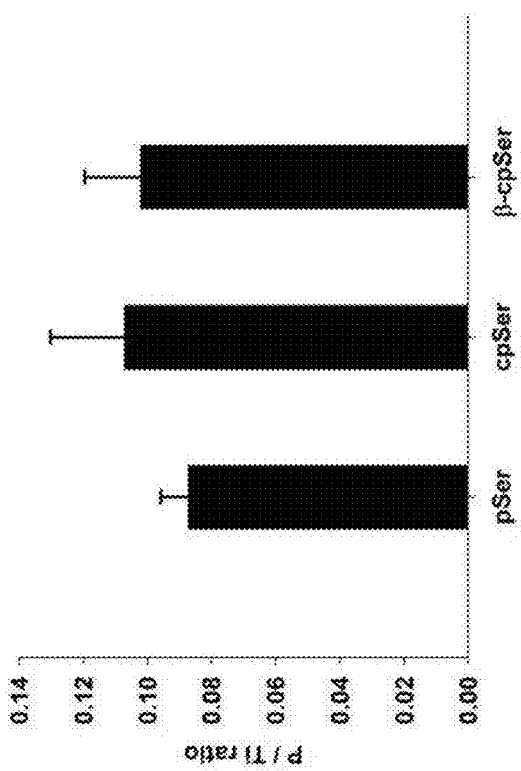

FIGS. 17A-17B. Atomic ratio of phosphorus to titanium (A) and atomic ratio of phosphorus and calcium to titanium analyzed by XPS for surfaces coated with pSer, cpSer and β-cpser peptides and incubated in calcium-phosphate solution for 24 hours at 37° C. (B).

DESCRIPTION OF SPECIFIC EMBODIMENTS OF THE INVENTION

The present invention, in some embodiments thereof, relates to functionalized titanium binding peptides and, more particularly, but not exclusively, to titanium binding peptides which are capable of promoting bone growth and mineralization.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Titanium is used as a material for coating implants due to its mechanical properties, good corrosion resistance and biocompatibility based on its chemical properties. However, titanium cannot bond directly to living bone after implantation. Since acidic amino acids have been proposed to be involved in the nucleation of calcium minerals and encourage calcium mineralization and since phosphoserine functional groups are known to have high affinity to oxide surfaces, the present inventors sought to develop a multi-functional peptidic coating for $TiO_2$ that would promote mineralization in order to improve implant-osseous integration.

The present inventors deduced rules which govern selection of such peptides. Thus, the peptide should comprise two functional moieties, the first being a titanium oxide binding moiety and the second a biologically functional moiety, wherein the first moiety has a higher affinity for titanium than the second. The first moiety should have a Beta sheet structure and the first and second moiety should be linked via a Beta sheet breaker linker.

Whilst reducing the present invention to practice, the present inventors synthesized an exemplary peptide—Pro-pSer-Trp-pSer-Trp-(Gly)$_3$-(Glu)$_5$ (SEQ ID NO: 1) and showed that it was capable of being strongly adsorped to a titanium surface.

Using sophisticated chromatographical analysis, the present inventors showed that the peptide was attached to the titanium oxide ($TiO_2$) surface via its phosphoserine residue (FIG. 7A). Further, it was shown that about one third of the peptide connected to carbonate molecules that were on the $TiO_2$ surface and two-thirds connected to the $TiO_2$ surface through pSer residue (FIG. 7B). This result was confirmed using X-ray photoelectron spectroscopy (XPS) measurements (FIGS. 8A-B).

Thus, according to one aspect of the present invention there is provided an isolated peptide comprising a titanium oxide binding amino acid sequence connected to a heterologous biologically active amino acid sequence via a beta sheet breaker linker, wherein:

(i) the titanium oxide binding amino acid sequence is selected to bind coordinatively with titanium oxide;

(ii) the titanium oxide binding amino acid sequence is selected to induce a beta sheet structure; and (ii) the titanium oxide binding amino acid sequence binds to titanium oxide with a higher affinity than the biologically active amino acid sequence binds to the titanium oxide under physiological conditions.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs.

The peptides of this aspect of the present invention are preferably no longer than 15 amino acids, no longer than 16 amino acids, no longer than 17 amino acids, no longer than 18 amino acids, no longer than 19 amino acids, no longer than 20 amino acids, no longer than 21 amino acids, no longer than 22 amino acids, no longer than 23 amino acids, no longer than 24 amino acids, no longer than 25 amino acids, no longer than 26 amino acids, no longer than 27 amino acids, no longer than 28 amino acids, no longer than 29 amino acids, no longer than 30 amino acids, no longer than 40 amino acids, no longer than 50 amino acids.

According to another embodiment the peptides of this aspect of the present invention are no longer than 100 amino acids, more preferably no longer than 90 amino acids, more preferably no longer than 80 amino acids, more preferably no longer than 70 amino acids, more preferably no longer than 60 amino acids, more preferably no longer than 50 amino acids, more preferably no longer than 40 amino acids, more preferably no longer than 30 amino acids, and more preferably no longer than 20 amino acids.

As mentioned, the peptides of this aspect of the present invention comprise two functional moieties attached to each other by a linker. Each of these components will be discussed individually below.

Titanium Oxide Binding Amino Acid Sequence

The term "titanium" as used herein includes metal titanium, titanium alloy, amorphous titanium dioxide, titanium dioxide anatase crystal, titanium dioxide rutile crystal and titanium dioxide brookite crystal.

It will be appreciated that under atmospheric conditions, the surface of titanium and its alloys become spontaneously covered with a nanometric oxide layer, composed mainly of $TiO_2$. In order to improve corrosion resistance and physiological reaction, this layer can be thickened by applying anodic potential. Thus, the titanium oxide binding peptide may bind titanium or an alloy of titanium.

The titanium oxide binding amino acid sequence preferably binds with titanium oxide with a Km of about 0.1-200 μM, or more preferably, 10-150 μM, 70-120 μM when tested in 10 mM TBS at a pH of about 7.4. According to a particular embodiment, the titanium oxide binding amino acid sequence binds with a Km of about 100 μM when tested in 10 mM TBS at a pH of about 7.4.

The titanium oxide binding amino acid sequence is selected such that it binds coordinatively to titanium (and not via electrostatic binding alone).

Thus, the present invention contemplates that the titanium oxide binding amino acid sequence comprises at least one of the following groups: a carboxyl group, a phosphate group, a phosphonate group and/or an L-dopa group.

According to one embodiment, the sequence is selected such that it forms a beta sheet secondary structure. Methods of selecting peptides that form a beta sheet secondary structure are disclosed in U.S. Patent Application No. 20100015197, incorporated herein by reference, as well as the peptides themselves.

Examples of primary amino acid sequences known to form a beta sheet secondary structure include alternating hydrophilic, negatively charged amino acids and hydrophobic amino acids—for example in a sequence X-Y-X-Y, where X is a hydrophobic amino acid and Y is a hydrophilic negatively charged amino acid.

It will be appreciated that X may not represent the same amino acid along the sequence, but a different hydrophobic amino acid and Y may not represent the same hydrophilic negatively charged amino acid, but a different one. For example, the sequence may be as set forth leucine-phosphoserine-valine-phosphotyrosine.

According to one embodiment, the core sequence X-Y is not repeated more than 7 times. Thus, the present invention contemplates repeating the X-Y core sequence twice, three times, four times, five times or six times.

Examples of hydrophobic amino acid include tyrosine, tryptophan, alanine, methionine, phenylalanine, leucine, proline, isoleucine, valine and glycine.

Examples of hydrophilic, negatively charged amino acids include phosphoserine, phosphotyrosine, phosphothreonine, glutamic acid and aspartic acid.

Phosphate compounds are utilized for surface modification of various transition metal oxides since they possess high binding strength. Phosphate, which appears as a free ion in physiological medium as well as in post translational modified biomolecules, coordinatively adsorbs to $TiO_2$ from aqueous media, displacing surface terminal hydroxyl groups, directly to titanium atoms. Further, it was shown that that phosphate groups bind stronger than carboxyls than amine groups to titanium oxide.

Thus, according to still another embodiment, at least one amino acid of the titanium oxide binding amino acid sequence is phosphorylated. Thus, for example, the present invention contemplates that at least one of the amino acids comprises phosphoserine, phosphothreonine or phophotyrosine.

According to a particular embodiment, the titanium oxide binding amino acid sequence comprises an alternating sequence of acidic amino acids and phosphoserine groups.

The present invention contemplates that the titanium oxide binding amino acid sequence is no longer than 20 amino acids. According to another embodiment, the titanium oxide binding amino acid sequence is no longer than 15 amino acids. According to still another embodiment, the titanium oxide binding amino acid sequence is no longer than 10 amino acids. According to another embodiment, the titanium oxide binding amino acid sequence is no longer than 5 amino acids.

The titanium oxide binding sequence may be as set forth by Z-X-Z-X, where Z is phosphoserine or L-dopa, where X is any hydrophobic amino acid, as listed herein above.

According to one embodiment, the first amino acid sequence of the titanium oxide binding sequence is a proline.

Contemplated titanium oxide binding amino acid sequences according to this embodiment are set forth in SEQ ID NOs: 22-26.

Thus, according to a particular embodiment the titanium oxide binding sequence is set forth by Pro-Z-X-Z-X (SEQ ID NO: 27), where X is any hydrophobic amino acid, as listed herein above and where Z is phosphoserine or L-dopa.

It will be appreciated that the titanium oxide binding sequence may also be able to bind to additional metals, metal oxides or even ceramics (e.g. magnesium oxide or calcium phosphate).

Thus, the peptides disclosed herein may also bind cobalt, cobalt alloys, chromium, chromium alloys, tantalum, tantalum alloys, stainless steel, zirconium, zirconium oxide, zirconium dioxide.

Linker:

As mentioned, the linker of the present invention is a β-sheet breaker linker. Typically, the linker provides a bend or turn at or near the junction between the two functional elements of the peptide. The linker which connects the first element to the second element is preferably a covalent bond (e.g. a peptide bond).

According to a particular embodiment, the conformational constraint is selected from the group consisting of, a proline or proline mimetic, an N alkylated amino acid, a double bond or triple bond or any other moiety which introduces a rigid bend into the peptide backbone.

In addition to proline, specific examples of moieties which induce suitable conformations include but are not limited to N-methyl amino acids such as sarcosine, hydroxy proline, anthranilic acid (2-amino benzoic acid) and 7-azabicyloheptane carboxylic acid.

The linker may comprise a single amino acid.

Examples of β-sheet breaker amino acid residues include, but are not limited to proline, glycine, lysine and serine (according to Chou and Fasman (1978) Annu. Rev. Biochem. 47, 258).

According to another preferred embodiment of this aspect of the present invention, the β-sheet breaker amino acid residue is a synthetic amino acid such as a Cα-methylated amino acid, which conformational constrains are restricted [Balaram, (1999) J. Pept. Res. 54, 195-199]. Unlike natural amino acids, Cα-methylated amino acids have a hydrogen atom attached to the $C_\alpha$, which affects widely their sterical properties regarding the ϕ and ψ angels of the amide bond. Thus, while alanine has a wide range of allowed ϕ and ψ conformations, α-aminoisobutyric acid (Aib, see Table 2, below) has limited ϕ and ψ conformations.

Alternatively, the linker of the present invention may comprise an amino acid sequence. The sequence may be 2, 3, 4, 5, 6 or 7 amino acids long. According to a particular embodiment the linker comprises the sequence $(Gly)_2$ or $(Gly)_3$.

According to another embodiment, the linker is a synthetic linker.

Biologically Active Amino Acid Sequence:

The biologically active amino acid sequence of the peptide of this aspect of the invention may comprise any biological activity, including, but not limited to a cell migration activity, an antimicrobial activity, an antibacterial activity, a cell homing activity, an osteoinducing (or osteoconducting) activity, an anti-inflammatory activity, a mineralizing activity, anti-adhesive activity, anti-thrombogenic activity.

It will be appreciated that the biologically active amino acid sequence is heterologous to the titanium binding amino acid sequence.

The qualifier "heterologous" when relating to the heterologous biologically active amino acid sequence indicates that the heterologous biologically active amino acid sequence is derived from a protein which does not normally comprise a titanium binding peptide to which it is fused so as to form the full-length peptide.

As used herein, the phrase "osteoinducing activity" refers to an ability to promote, induce, conduct, stimulate, generate, or otherwise effect the production of bone or the repair of bone. The osteoinducing activity may elicit an effect on the repair of the defect in terms of shortening the time required to repair the bone, by improving the overall quality of the repair, where such a repair is improved over situations where there is a lack of osteoinducing activity, or may achieve contemporaneously both shortened repair times and improved bone quality. It is appreciated that osteogenic agents may effect bone production or repair by exploiting endogenous systems, such as by the inhibition of bone resorption.

Osteoinducing peptides may promote bone growth by acting as bone anabolic agents. Osteoinducing peptides may also affect repair of the bone defect by stabilizing the defect to promote healing. The ramifications of using such osteoinducing peptides include increased healing rates, effecting a more rapid new bone ingrowth, improved repair quality, or improved overall quality of the resulting bone.

In one embodiment the peptide is a full length or biologically active fragment of bone morphogenetic proteins (BMPs), such as BMP-2, BMP-4, BMP-6, BMP-7, BMP-9, BMP-12, BMP-13 and BMP-14, chrysalin, osteogenic growth peptide (OGP), bone cell stimulating factor (BCSF), KRX-167, NAP-52, gastric decapeptide, parathyroid hormone (PTH), a fragment of parathyroid hormone, osteopontin, osteocalcin, a fibroblast growth factor (FGF), such as basic fibroblast growth factor (bFGF) and FGF-1, osteoprotegerin ligand (OPGL), platelet-derived growth factor (PDGF), an insulin-like growth factor (IGF), such as IGF-1 and IGF-2, vascular endothelial growth factor (VEGF), transforming growth factor (TGF), such as TGF-alpha and TGF-beta, epidermal growth factor (EGF), growth and differentiation factor (GDF), such as GDF-5, GDF-6, and GDF-7, thyroid-derived chondrocyte stimulation factor (TDCSF), vitronectin, laminin, amelogenin, intergrin, collagen and amelin.

Fibrinogen and biologically active fragments thereof are also known to act as osteoinducing peptides, as well as fibronectin and biologically active fragments thereof (e.g. RGD or RGE).

Acidic amino acid sequences are also known to be osteoinductive. Thus, for example the present invention contemplates a biologically active amino acid sequence comprising at least 3, at least 4 or at least 5 negatively charged acidic amino acids (e.g. $(Glu)_5$(SEQ ID NO: 7) or $(Asp)_5$(SEQ ID NO: 11).

Preferably, the osteoconductive amino acid sequence comprises 3, 5 or 7 negatively charged acidic amino acids.

According to still another embodiment, the negatively charged acidic amino acid sequence is no longer than 15 amino acids.

According to still another embodiment, the negatively charged acidic amino acid sequence is no longer than 100 amino acids.

Non-thrombogenic or anti-adhesive amino acid sequences include for example tissue plasminogen activator, reteplase, TNK-tPA and glycoprotein IIb/IIIa inhibitors.

Preferably, the biologically active amino acid sequence is no longer than 100 amino acids, more preferably no longer than 90 amino acids, more preferably no longer than 80 amino acids, more preferably no longer than 70 amino acids, more preferably no longer than 60 amino acids, more preferably no longer than 50 amino acids, more preferably no longer than 40 amino acids, more preferably no longer than 30 amino acids, more preferably no longer than 20 amino acids, and even more preferably no longer than 10 amino acids.

It will be appreciated that the titanium oxide binding amino acid sequence binds to titanium oxide with a higher affinity than the biologically active amino acid sequence when measured under identical conditions. Preferably, the titanium oxide binding amino acid sequence binds to titanium oxide with at least 1.2 the affinity than the biologically active amino acid sequence binds to titanium oxide. More preferably, the titanium oxide binding amino acid sequence binds to titanium oxide with at least 1.4 times the affinity than the biologically active amino acid sequence binds to titanium oxide. More preferably, the titanium oxide binding amino acid sequence binds to titanium oxide with at least 1.5 times the affinity than the biologically active amino acid sequence binds to titanium oxide. More preferably, the titanium oxide binding amino acid sequence binds to titanium oxide with at least twice times the affinity than the biologically active amino acid sequence binds to titanium oxide. More preferably, the titanium oxide binding amino acid sequence binds to titanium oxide with at least three times the affinity than the biologically active amino acid sequence binds to titanium oxide. More preferably, the titanium oxide binding amino acid sequence binds to titanium oxide with at least three times the affinity than the biologically active amino acid sequence binds to titanium oxide. More preferably, the titanium oxide binding amino acid sequence binds to titanium oxide with at least four times the affinity than the biologically active amino acid sequence binds to titanium oxide. More preferably, the titanium oxide binding amino acid sequence binds to titanium oxide with at least five times the affinity than the biologically active amino acid sequence binds to titanium oxide. More preferably, the titanium oxide binding amino acid sequence binds to titanium oxide with at least ten times the affinity than the biologically active amino acid sequence binds to titanium oxide.

Selection of which titanium oxide binding amino acid sequence to pair with which biologically active amino acid sequence may be performed by testing the binding of each of the sequences individually to a titanium oxide surface. This may be effected by as indicated by performing dissolution tests (differences in pH ionic strength and hydrophobicity of eluting agents).

Care should also be taken when pairing the functional moieties that the biologically active amino acid sequence does not interfere with the binding of the titanium oxide binding amino acid sequence. Conversely, care should also be taken that the titanium oxide binding amino acid sequence does not interfere with the biological activity of the biologically active amino acid sequence.

Thus, for example a contemplated pair for a peptide of the present invention comprises pSer-Trp-pSer-Trp- (SEQ ID NO: 2) as the titanium oxide binding amino acid sequence and $(Glu)_5$ (SEQ ID NO: 7) as the biologically active (in this case osteoinducing) activity. Thus a contemplated peptide of the present invention is as set forth in Pro-pSer-Trp-pSer-Trp-$(Gly)_3$-$(Glu)_5$ (SEQ ID NO: 1).

Another contemplated pair for a peptide of the present invention comprises pSer-Phe-pSer-(SEQ ID NO: 3) as the titanium oxide binding amino acid sequence and $(Glu)_3$ as the biologically active (in this case osteoinducing) activity. Thus another contemplated peptide of the present invention is as set forth in Pro-pSer-Phe-pSer-$(Gly)_2$-$(Glu)_3$ (SEQ ID NO: 4).

Another contemplated pair for a peptide of the present invention comprises L-DOPA-X-L-DOPA-X-(SEQ ID NO: 5) as the titanium oxide binding amino acid sequence and (Glu)$_5$ (SEQ ID NO: 7) as the biologically active (in this case osteoinducing) activity, where X is any hydrophobic amino acid, as set forth herein above.

The two functional domains of the peptide of the present invention may be connected through any orientation. Thus, for example, the N terminus of the titanium oxide binding amino acid sequence may be connected to the C terminus of the biologically active amino acid sequence. Alternatively, the C terminus of the titanium oxide binding amino acid sequence may be connected to the N terminus of the biologically active amino acid sequence.

As mentioned the sequences of the peptides of this aspect of the present invention may comprise modifications. Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (No1), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |

TABLE 2-continued

| Non-conventional amino acid | Code | Non-conventional amino acid | Code |
|---|---|---|---|
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmas | N-cycloundecylglycine | Ncund |
| D-α-methylasparatate | Dnmas | N-(2,2-diphenylethyl)glycine | Nbhm |
| D-α-methylcysteine | Dnmcy | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmor | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmor | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |

TABLE 2-continued

| Non-conventional amino acid | Code | Non-conventional amino acid | Code |
|---|---|---|---|
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L- α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenylethyl-amino)cyclopropane | Nmbc | | |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

Thus, the present invention contemplates peptides having a sequence homology at least 80% identical, more preferably at least 85% identical, more preferably at least 90% identical, more preferably at least 91% identical, more preferably at least 92% identical, more preferably at least 93% identical, more preferably at least 94% identical, more preferably at least 95% identical, more preferably at least 96% identical, more preferably at least 97% identical, more preferably at least 98% identical, more preferably at least 99% identical to the sequences as set forth in SEQ ID NOs: 1-20 as determined using BlastP software of the National Center of Biotechnology Information (NCBI) using default parameters). In measuring homology between a peptide and a protein of greater size, homology is measured only in the corresponding region; that is, the protein is regarded as only having the same general length as the peptide, allowing for gaps and insertions.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl) (benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such as decreased degradation or clearance; decreased repulsion by various cellular pumps, improve immunogenic activities, increased specificity, increased affinity, decreased toxicity and the like.

The peptides of the invention may be linear or cyclic (cyclization may improve stability, or uptake into the microbe). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the peptides of the present invention can also be synthesized using in vitro expression systems. These methods are well known in the art and the components of the system are commercially available.

As mentioned, the peptides of this aspect of the invention may be useful for coating devices such as implants and surgical instruments.

According to one embodiment, the surface of the device is coated with titanium or zirconium oxide.

The device may comprise additional metals, metal oxides or other components such as ceramics, including but not limited to cobalt, cobalt alloys, chromium, chromium alloys, tantalum, tantalum alloys, stainless steel, zirconium, zirconium oxide, zirconium dioxide, magnesium oxide and calcium phosphate.

The peptides may be attached to the surface of the implant using any method known in the art including spraying, wetting, immersing, dipping, painting, ultrasonic welding, welding, bonding or adhering or otherwise providing a surface with the peptides of the present invention. Typically, the peptides of the present invention self-assemble on the surface.

The peptides of the present invention may be attached as monolayers or multiple layers.

The amount of peptide applied to the surface can vary depending on the desired outcome. Thus, for example, the present invention contemplates adjusting the ability of a device to promote bone growth or osseointegration by varying the surface density of an osseoinducing peptide of the present invention on the device. Increasing the surface density of the peptide may increase the ability of the device to promote bone growth or osseointegration compared to devices having a lower surface density of peptide.

Similarly, decreasing the surface density of the peptide on the device decreases the ability of the device to promote bone growth or osseointegration. By varying the surface density of the peptide, devices can be tailored to the needs of a specific patient to obtain the amount of bone growth or osseointegration needed by the patient.

The peptide can be passively adsorbed to the device for example by incubating the implant in 0.4 mg/ml in Tris-buffered saline (TBS) for about 1 hour. Alternatively, the peptide can be suspended in a vehicle and applied to the device. Typically, the vehicle is a pharmaceutically acceptable vehicle that contains a binding agent, for example a gel or thickener that causes the peptide to adsorb or adhere to the surface of the device.

It will be appreciated that the surface may be pre-treated prior to coating with the peptide of the present invention using any method known in the art in order to enhance peptide adsorption or for any other purpose.

An "implant" as used herein refers to any object intended for placement in a human body that is not a living tissue. The implant may be temporary or permanent. The implant is typically a device comprising artificial components.

Titanium implants may be used for a variety of purposes, listed herein below and the present invention contemplates coating these devices with the peptides of the present invention.

Bone and Joint Replacement: About one million patients worldwide are treated annually for total replacement of arthritic hips and knee joints. The prostheses come in many shapes and sizes. Hip joints normally have a metallic femoral stem and head which locates into an ultrahigh molecular weight low friction polyethylene socket, both secured in position with polymethyl methacrylate bone cement. Some designs, including cementless joints, use roughened bioactive surfaces (including hydroxyapatite) to stimulate osseointegration, limit resorption and thus increase the implant lifetime for younger recipients. Internal and external bone-fracture fixation provides a further major application for titanium as spinal fusion devices, pins, bone-plates, screws, intramedullary nails, and external fixators.

According to the teachings of the present invention various types of bones can be formed and/or repaired using the presently described methods, these include without being limited to, ethmoid, frontal, nasal, occipital, parietal, temporal, mandible, maxilla, zygomatic, cervical vertebra, thoracic vertebra, lumbar vertebra, sacrum, rib, sternum, clavicle, scapula, carpal bones, ilium, ischium, pubis, patella, calcaneus, and tarsal bones. The present invention also contemplates generation of long bones (i.e. bones which are longer than they are wide and grow primarily by elongation of the diaphysis with an epiphysis at the ends of the growing bone). Examples of long bones include femur, tibia, fibula (i.e. leg bones), humerus, radius, ulna (i.e. arm bones), metacarpal, metatarsal (i.e. hand and feet bones), and the phalanges (i.e. bones of the fingers and toes).

Since the implants of the present invention may be used to generate tissue thereon, they may be used for treating diseases characterized by tissue damage or loss (e.g. bone or connective tissue loss).

As used herein, the term "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the phrase "pathology characterized by bone or connective tissue damage or loss" refers to any disorder, disease or condition exhibiting a bone or connective tissue damage (i.e., non-functioning tissue, cancerous or pre-cancerous tissue, broken tissue, fractured tissue, fibrotic tissue, or ischemic tissue) or a bone or connective tissue loss (e.g., following a trauma, an infectious disease, a genetic disease, and the like) which require tissue regeneration. Examples for disorders or conditions requiring bone or connective tissue regeneration include, but are not limited to, bone cancer, articular cartilage defects, musculoskeletal disorders, including degenerative disc disease and muscular dystrophy, osteoarthritis, osteoporosis, osteogenesis, Paget's disease, bone fractures, and the like.

As used herein, the term "subject" refers to mammals, including humans. Preferably, this term encompasses individuals who suffer from pathologies as described hereinabove.

Preferably the implant is implanted at a ligament, tendon, cartilage, intervertebral disc or bone tissue.

Thus for example, when administration of the implant is for bone regeneration, the scaffold is placed at a desired location in bone in such conditions such as non-union fractures, osteoporosis, of periodontal disease or defect, osteolytic bone disease, post-plastic surgery, post-orthopedic implantation, post neurosurgical surgery that involves calvaria bone removal, in alveolar bone augmentation procedures, for spine fusion and in vertebral fractures.

When the administration of the implant is for generation of tendon/ligament tissue, the implant is placed at a desired location in tendon/ligament following tissue tear due to trauma or inflammatory conditions.

When the administration of the implant is for generation of cartilage tissue, the scaffold is placed at a desired location in cartilage to treat defects due to Rheumatoid Arthritis, Osteoarthritis, trauma, cancer surgery or for cosmetic surgery.

When the administration of the implant is for generation of intervertebral disc tissues including nucleous pulposus and annulus fibrosus, the scaffold is placed at a desired location of nucleous pulposus degeneration, annulus fibrosus tears, or following nucleotomy or discectomy.

Dental Implants: A major change in restorative dental practice worldwide has been possible through the use of titanium implants. A titanium 'root' is introduced into the jaw bone with time subsequently allowed for osseointegration. The superstructure of the tooth is then built onto the implant to give an effective replacement. Dental implants can be used to treat or repair damaged or missing teeth, and facial bones. In certain embodiments, the dental implant can be entirely for aesthetic purposes. In addition, implants can be use as a filler to augment or form dental tissue as to support the function of natural tissues (such as teeth or bone) or artificial prosthesis.

Maxillo and Cranio/facial treatments: Surgery to repair facial damage using the patients own tissue cannot always obtain the desired results. Artificial parts may be required to restore the ability to speak or eat as well as for cosmetic appearance, to replace facial features lost through damage or disease. Osseointegrated titanium implants meeting all the requirements of bio-compatibility and strength have made possible unprecedented advances in surgery, for the successful treatment of patients with large defects and hitherto highly problematic conditions.

Cardiovascular devices Titanium is regularly used for pacemaker cases and defibrillators, as the carrier structure for replacement heart valves, and for intra-vascular stents. External Prostheses Titanium is suitable for both temporary and long term external fixations and devices as well as for orthotic calipers and artificial limbs, both of which use titanium extensively for its light weight, toughness and corrosion resistance. Thus, for example, the present invention therefore envisions coating vascular stents with the peptides of the present invention. The peptides may serve to repel or attract specific type of proteins in cells which may affect the cell cycle of endothelial cells in contact with the surface to reduce or prevent restenosis, or general type of implants coated by the method of the present invention to achieve beneficial effect in the integration of the implant with tissue.

Surgical Instruments: A wide range of surgical instruments are made in titanium. The metal's lightness is a positive aid to reducing any fatigue of the surgeon. Instruments are frequently anodised to provide a non reflecting surface, essential in microsurgical operations, for example in eye surgery. Titanium instruments withstand repeat sterilization without compromise to edge or surface quality, corrosion resistance or strength. Titanium is non magnetic, and there is therefore no threat of damage to small and sensitive implanted electronic devices.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Materials: $TiO_2$ particles (10 μm, Sachtleben, Duisburg, Germany). Analytical-grade sodiumacetate, Trizma base (Tris) and sodium hydroxide (Sigma, St. Louis, Mo.), sodium chloride, sodium phosphate and hydrochloric acid (Merck, Dermstadt, Germany), and HPLC-grade acetonitrile (Sigma, St. Louis, Mo.) were used for the chromatographic adsorption and desorption solutions. Water was purified by the Milli-Q system (Millipore, Bedford, Mass.) to 18.2 MΩ3 cm.

Figure 3:
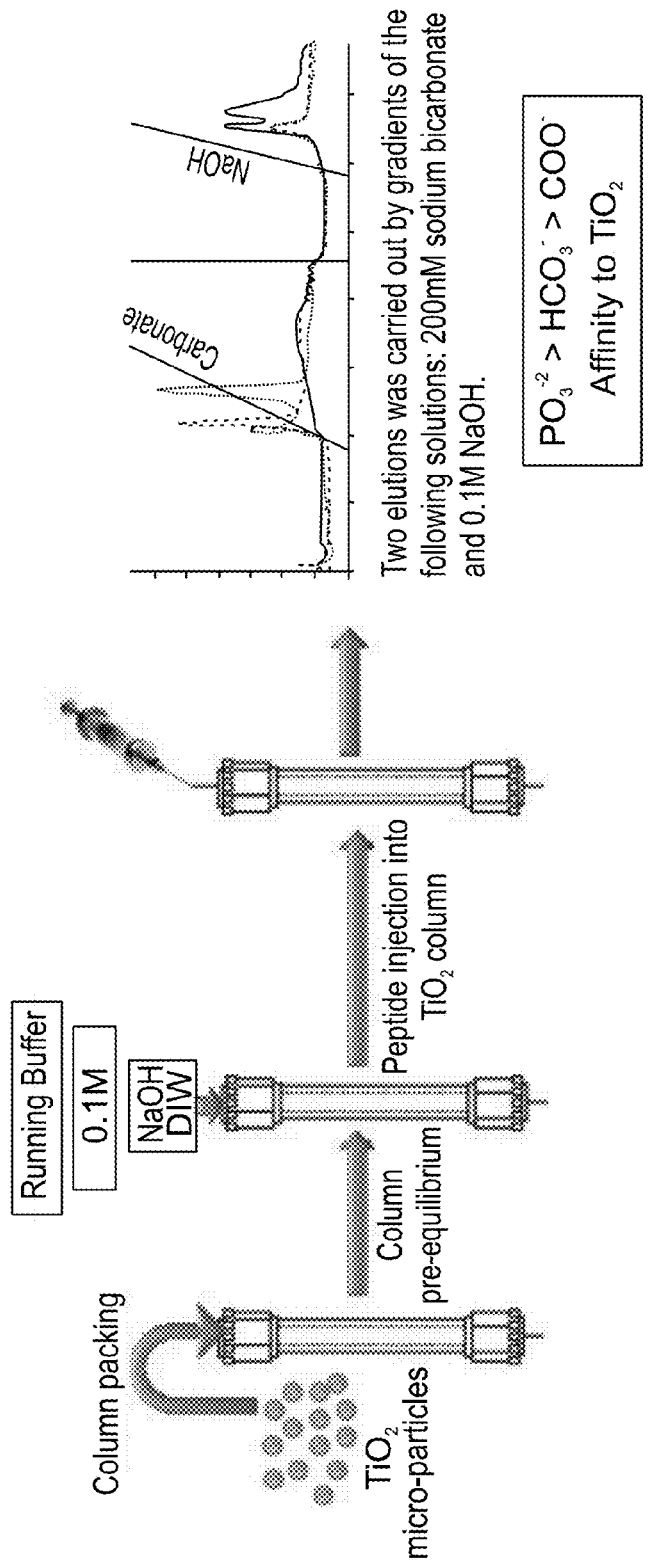

Chromatography on $TiO_2$ Surfaces: as described in Golan Gertler, Gideon Fleminger and Hanna Rapaport. Langmuir 2010, 26(9), 6457-6463, and further illustrated in FIG. 3. Stainless steel (4.6_50 mm) column was packed with $TiO_2$ anatase (Sachtopore NP 10μ/100 A°, particle size/pore size respectively) suspended in methanol. The packed columns were washed consecutively with water and 0.1 M NaOH to desorb surface contaminants. The columns were then pre-equilibrated with the running buffer. Lyophilized peptides were dissolved in the running buffer (0.2 mg/mL) and centrifuged at 5000 g for 5 min prior to injection into the column to remove possible aggregates. The supernatants (100 μL) were injected on to the $TiO_2$ column at a flow rate of 0.02 mL/min to attain 40 min retention time for adsorption. After 65 minutes, the flow rate was increased to 0.5 mL/min. Ten millimolar Tris and phosphate buffer solutions, pH 7.4, were used as adsorption (running) media. In addition, these buffers complemented by 150 mM NaCl (TBS, PBS, respectively) were also examined. Elution was carried out by gradients of the following solutions applied consecutively to the column: 1 M NaCl, 80% acetonitrile, 200 mM sodium phosphate, and 0.1 M NaOH, monitored at 215-280 nm. The chromatograms were obtained at room temperature using 0.2 μm filtered (Millipore, Badford, Mass.) solutions.

Revised simulated body fluids (SBF) solution was prepared according to Oyane et. al., with the following ion concentrations: $Na^+$ 142 mM, $K^+$ 5 mM, $Mg^{2+}$ 1.5 mM, $Ca^{2+}$ 2.5 mM, $Cl^-$ 103 mM, $HCO_3^-$ 27 mM, $HPO_4^{2-}$ 1 mM $SO_4^{2-}$ 0.5 mM.

$TiO_2$ Surface Preparation: as described in Catherine D. Reyes, Timothy A. Petrie, Kellie L. Burns, Zvi Schwarts and Andres J. Garcia. (2007) Biomaterials 28(21): 3228-323.

Surfaces were prepared by Thermal Evaporation—microscope slides were coated with pure 99.9% Ti particles to 40 nm thickness. Oxide layer was promoted by heating the slides for 8 hours on 180° C.

Figure 1A:
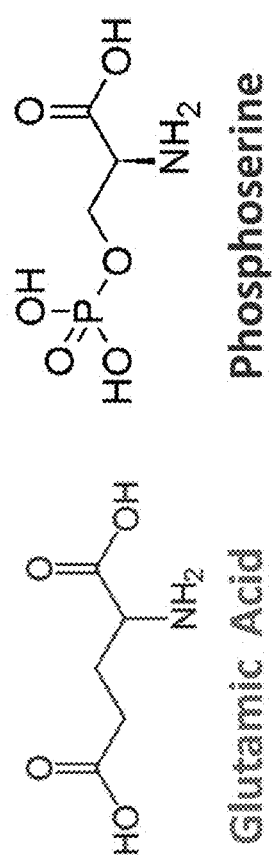
Figure 1B:
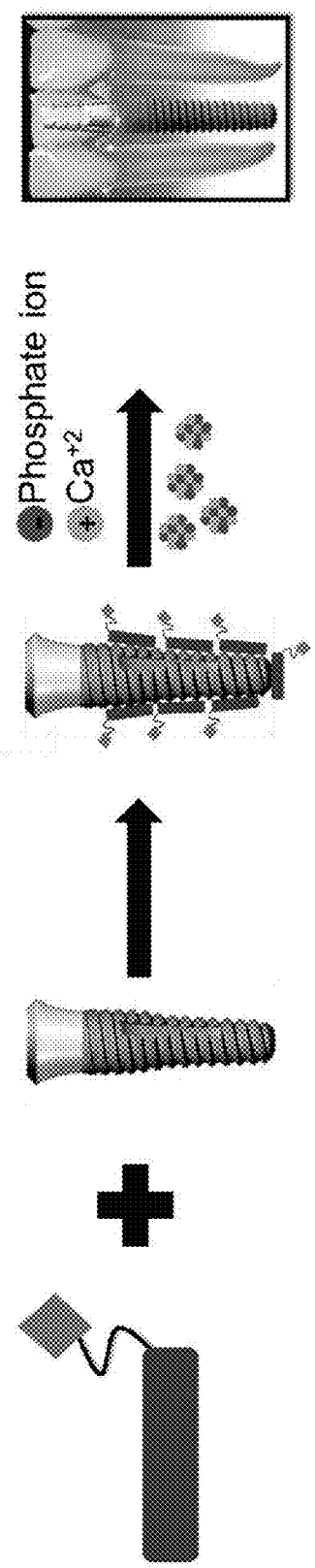
Figure 2:
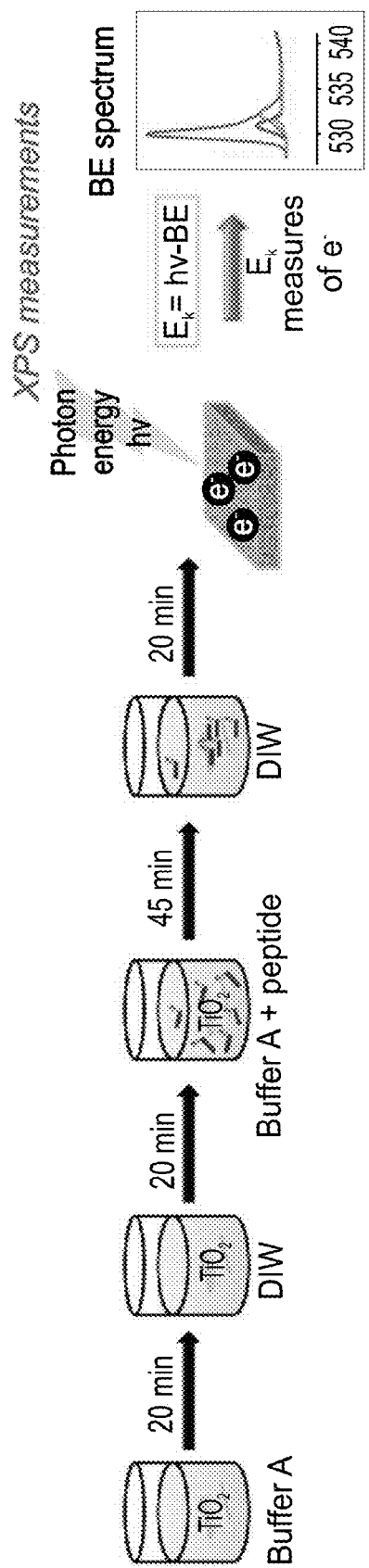

Peptide binding to $TiO_2$ surfaces: as set forth in FIG. 2.

Peptide: The peptide Pro-pSer-Trp-pSer-Trp-$(Gly)_3$-$(Glu)_5$ (SEQ ID NO: 1), also referred to as PpSer was synthesized using common automated peptide synthesis techniques. The β-strand peptides were obtained as lyophilized powder at >95% purity level (determined by reversed phase HPLC). The acidic peptides were solubilized using 10 mM NaOH solution followed by bath sonication and centrifugation at 5000 g for 8 minutes to remove possible aggregates.

A schematic illustration of the peptide is presented in FIG. 5.

Results

The peptide dissolved in two different running buffer, Tris buffer saline (TBS) and sodium bicarbonate saline (BCS). The affinity of functional groups to $TiO_2$ from previous works was known to be $PO_4^{-3}$ > $HCO_3^-$ > $COO^-$. (The diagonal line in the chromatography is the elution gradient: 0-200 mM sodium bicarbonate & 0-0.1M NaOH).

Peptides that bind to $TiO_2$ only through Glutamic acid functional groups will elute in BC gradient, however peptides that bind to $TiO_2$ through pSer functional groups will elute in the NaOH gradient.

As illustrated in FIG. 7A, the peptide bonded to $TiO_2$ through pSer functional groups in TBS buffer. The peptide is most likely bound to the surface through phosphate groups.

The idea behind using BCS as running buffer is to block the surface with carbonate ions before the peptide injection. This way the phosphate groups, that have a higher affinity to the surface, can displace the carbonate ion and bond to the $TiO_2$ surface while the Glu tail stays free—as can be seen from the chromatography results presented in FIG. 7B, ⅔ of the peptide was able to displace the carbonate ions. ⅓ of the peptide can't displace the carbonate ions and bonded to them through hydrogen bonds therefore they eluted at BC gradient.

XPS Analysis of Peptide on $TiO_2$ (Early Stages of Mineralization):

The results are presented in FIGS. 8A-B and summarized in Table 3, herein below. Shown are the XPS atomic ratios of $TiO_2$, peptide diluted in TBS bonded on $TiO_2$, peptide diluted in BCS bonded on $TiO_2$ and all the slides after 40 minutes in SBF1.5 (c).

TABLE 3

| Atomic Ratio | $TiO_2$* | TBS + $P_{pSer}$* | BCS + $P_{pSer}$* | $TiO_2$SBF** | TBS + $P_{pSer}$SBF** | BCS + $P_{pSer}$SBF** | SBF Results |
|---|---|---|---|---|---|---|---|
| Ca/P | — | — | — | 1.72 | 0.835 | 1.80 | Adsorption kinetics of $Ca^{+2}$ |
| Ti/Ca | — | — | — | 5.28 | 28.42 | 9.67 | to carbonate ions and to $TiO_2$ surface through electrostatic interactions is faster than the mineralization process |
| Ti/P | — | 23.67 | 58.52 | 9.10 | 23.74 | 17.45 | The P concentration in TBS buffer belongs to the peptide |
| C/P | — | 29.95 | 181.28 | 45.43 | 36.84 | 132.06 | C concentration increase thanks to SBF solution. |

At pH = 7.4 $TiO_2$ surface is negatively charge
*The peptide dissolved in two different running buffers, TBS and BCS, and bonded to $TiO_2$ slides. The carbonate-phosphate (C/P) ratio in TBS buffer is the indication of a bound peptide on the surface- the peptide contains 64 C and 2 P - 31:1. In BCS this ratio is higher because C concentration increases thanks to carbonate ions.
**The $TiO_2$ + peptide complex after being 40 min in SBF (simulated body fluids).

TBS:

From Ti/P ratio it can be seen that the P belongs to the peptide.

From Ca/P ratio it can be seen that the area on the surface that didn't bind peptide is negatively charge, therefore there is $Ca^{+2}$ adsorption to the surface.

C/P ratio is bigger because C concentration increases thanks to SBF solution.

BCS: Ti/P ratio becomes smaller because the P concentration is increases thanks to the mineralization process that started.

Ca/P ratio indicates that the $Ca^{+2}$ ions adsorb immediately both to $TiO_2$ surface and to the peptide coated surfaces. Differences point to peptide effect on calcium adsorption; for example Ca/P ratio in sample prepared in TBS buffer is close to 1 as expected by the interactions between 5 carboxyls that would be neutralized on average by 2.5 calcium ions versus the number of phosphate ions in the peptide (2).

Inductively Coupled Plasma Mass Spectrometry (ICP-MS) Results

The results are illustrated in FIG. 9 and Table 4 herein below.

TABLE 4

| ratio | TBS | CBS | Ti |
|---|---|---|---|
| Ca/P | 1.38 | 1.46 | 1.38 |

It can be seen from the ICP results, that surface+peptide TBS has lower amounts of Ca,P than surface+peptide BCS. Therefore the carbonate ions affects the peptide and from this it can be concluded that the Glu tail can change its position as a response to the surrounding—a proof that the peptide is bi-functional.

Chromatographic Analysis of PF1, PF2, PF4, PF6 and PF8 on $TiO_2$ Anatase Column The following peptides were analyzed chromatographically on a $TiO_2$ anatase column—Pro-Asp-(Phe-Asp)$_n$, n=1, 2, 4, 6 and 8, (SEQ ID NO: 20) denoted $P_{F1}$, $P_{F2}$, $P_{F4}$, $P_{F6}$ and $P_{F8}$. These peptides are known to have a B sheet structure.

Results

The results are presented in FIGS. 10A-B. The results illustrate the effect of peptide length on binding efficiency for peptides designed to assume the beta-sheet structure—thus demonstrating that there is a link between the designed sequence and the efficiency of binding.

Example 2

Materials and Methods

Peptides:

The peptides Pro-Ser(phos)-Phe-Ser(phos)-Trp-(Gly)$_3$-(Glu)$_5$ denoted 'pSer' (SEQ ID NO: 12) and Pro-pSer-Phe-pSer-Trp-(Gly)$_3$ denoted 'cpSer' (SEQ ID NO: 13) was synthesized and purified by high performance liquid chromatography (HPLC) to >95% (Cambridge Research Biochemical). The peptide Pro-Ser(phos)-Ser(phos)-Phe-Trp-(Gly)$_3$ denoted 'β-cpSer', (SEQ ID NO: 14) was synthesized and purified by HPLC to >95% (Caslo). $TiO_2$ particles (10 μm, Sachtleben, Duisburg, Germany) had a surface area of 62.4 $m^2g^{-1}$. Unless otherwise specified, all reagents were purchased from Sigma-Aldrich (Rehovot, Israel) and were of the highest available purity. Sodium hydroxide, sodium bicarbonate, potassium phosphate and calcium chloride dehydrate. Tris-buffer saline (TBS) was prepared with Trizma™ base (10 mM) and NaCl (154 mM) adjusted to pH 7.50 with 0.1 M HCl. All solutions were prepared with deionized water (DIW) (18.2 MΩ×cm, Direct Q-5 Merck Millipore, Billerica, Mass.).

Circular Dichroism (CD) Spectroscopy:

Circular dichroism (CD) measurements were performed to characterize the secondary structure of peptides in aqueous solution. Spectra in the range of 190-260 nm were recorded at room temperature on a Jasco J-715 spectropolarimeter (Tokyo, Japan), using a 1 mm quartz cuvette. Peptides solutions were prepared by dissolving peptide's lyophilized powders in TBS to concentrations of 0.2 and 0.4 mg ml$^{-1}$. Data are reported as mean molar ellipticity per residue [deg cm$^2$ dmol$^{-1}$ residue$^{-1}$].

Attenuated Total Reflection (ATR-FTIR) Spectroscopy

Samples of 1 mg ml$^{-1}$ peptides were prepared by dissolving peptide powder into TBS and were deposited on ZnSe 45° trapezoid prism (REFLEX Analytical Corporation) and dried at 37° C. to form a film that is macroscopically thick. The FTIR spectra reported here were all recorded using a Nicolet 6700 FTIR spectrometer (Thermo Scientific) fitted with a narrow-band liquid nitrogen cooled MCT detector. The spectra were recorded in the range from 4000 to 600 cm-1, 4-1 resolution and 244 scans. The FTIR data were collected using the OMNIC software. After collection the spectra were corrected for distortion using atmospheric suppression (to minimize infrared absorption by $CO_2$ and water vapor in the ambient air). A baseline correction function was applied to all spectra. Reference spectra were measured using the bare ZnSe prism.

Chromatography:

A stainless steel (4.6×50 mm) column was packed with $TiO_2$ anatase (Sachtopore NP 10μ/100 Å, particle size/pore size respectively) suspended in methanol. The packed column was washed consecutively with water and 0.1 M NaOH to desorb surface contaminants. The column was then pre-equilibrated with the loading/running buffer. The chromatographic process was performed on a HPLC system (Algient Technologies, 1260 Infinity, Germany). Peptides dissolved in the loading/running buffer (0.4 mg/ml) were sonicated for 10 minutes and centrifuged at 145000 rpm for 8 minutes and were injected to the $TiO_2$ column at a flow rate of 0.02 ml/min to attain ~40 minutes retention time for adsorption. 10 mM tris buffered saline pH 7.4 (TBS) was used as adsorption/running media. After 65 minutes, the flow rate was increased to 0.5 ml/min. Elution was carried out by gradients of 200 mM sodium bicarbonate solution pH 7.4 and 0.1 M NaOH. Elution was monitored at 280 nm. All solutions were filtered using 0.2 μm filters (Millipore, Badford, Mass.).

Adsorption Isotherm:

The adsorption of all three peptides to $TiO_2$ particles were measured with peptides solution in a range of concentrations from 0.002 to 0.524 mM in 10 mM TBS solution. $TiO_2$ particles were suspended in TBS 10 mM, pH 7.4, to a final concentration of 1.8 mg/ml. To each test tube containing 0.5 ml of peptide at different concentrations, 0.5 ml of $TiO_2$ particles solution was added. The samples were continuously mixed with a tube rotator for 1 h at room temperature. To precipitate the $TiO_2$ particles, the test tubes were centrifuged at 5000 rpm for 3 minutes and the absorption of the supernatant was measured at 280 nm using a microplate-reader (BioTek instruments). Peptide concentration was determined based on calibration curve of each peptide prepared in TBS solution. In order to describe the adsorption of molecules on $TiO_2$ particles surface the sips equation, also known as the Langmuir-Freundlich equation (1), was used:

$$S = \frac{S_{max}(kC)^\alpha}{1 + (kC)^\alpha} \quad (1)$$

where S is the amount of adsorbed molecules (mol m$^{-2}$), $S_{max}$ is the maximum amount of molecules adsorbed (mol m$^{-2}$), C is their concentration is solution at equilibrium (mM), k is the association coefficient (M$^{-1}$) and α is the constant representing this distribution.[30]

Preparation of TiO$_2$ Surfaces

Titanium coated silicon wafers and Borosilicate glass slides (Pgo, Germany) were prepared in the nanofabrication facility of BGU. The titanium (99.995%, Kurt J. Lesker) was evaporated thermally at a pressure equal to 2.8*10$^{-7}$ mbar using a thermal evaporator (Odem LTD, Rehovot, Israel) to thickness of 40 nm. Prior to coating, the substrates were cleaned in acetone and isopropanol. Next, these were subjected to oxygen plasma cleaning for 7 minutes (0.4 mbar of oxygen pressure in chamber). After the coating process, all surfaces were placed on a heating plate at 180° C. for 8 hours[31]. Silicon coated surfaces were cut to 1×0.5 cm$^2$ using ADT7100 icing saw. The surfaces were characterized for titanium dioxide (TiO$_2$) by XPS. XPS spectra were measured using ESCALAB 250 spectrometer with Al X-ray source and monochromator. General survey and high-resolution spectra of elements were recorded. Calibration of the peaks position was performed according to the position of the C1s line (284.8 eV). The Ar-etching was done under the pressure of 1×10-8 mbar using the ion source with 3 μA 2 kV power and the rate of sputtering was 6 A/sec.

TiO$_2$ Surface Coating:

Surfaces were incubated in TBS solution for 45 min in room temperature, and then the surfaces were incubated in 0.4 mg ml$^{-1}$ peptide-TBS 10 mM solution for 1 hr at room temperature and were dried with nitrogen. Peptide coating were analyzed by XPS.

Calcium-phosphate Adsorption on Coated Surfaces:

The ability to absorb calcium-phosphate (Ca—P) ions by the different peptide coatings were measured using Ca—P solution. The solution was prepared at physiological pH and contained K$_2$HPO$_4$ (1.0 mM), CaCl$_2$.2H$_2$O (2.5 mM), dissolved consecutively in deionized water at 37° C. and buffered at pH ~7.4 using 50 mM Trizma™ base and an appropriate volume of 1M HCl. Coated surfaces were incubated in Ca—P solution at 37° C. for 24 h.

Results

The designed bifunctional peptide, 'pSer' (FIG. 11A) features a binding motif to titanium oxide and a stretch of negatively charged amino acids intended to induce adsorption of calcium to promote calcified mineralization. The titanium oxide binding motif was designed to induce the β-pleated structure with two phosphoserine amino acids decorating the hydrophilic face of this binding region. Trp and Phe residues were chosen to be the alternating hydrophobic amino acids to assist in peptide detection by spectroscopy. This binding motif segment is followed by a linker of three Gly residues and five consecutive negatively charged Glu amino acids. A peptide (FIG. 11B) lacking the stretch of the Glu residues, denoted 'cpSer', was also studied as a control to assess the effect of the Glu tail on the structure of the peptide and on the calcium adsorption. A third peptide (FIG. 11C) lacking the β-pleated structure at the binding motif denoted 'β-cpSer', was also studied as a control to the β-pleated structure on the affinity to titanium oxide.

CD measurements provided information on peptide conformation in the solution used for the spontaneous adsorption of the peptides to the titanium oxide. All peptides showed random coil conformation in 10 mM TBS buffer at physiological pH over the 0.2-0.4 mg ml$^{-1}$ range of concentrations (FIG. 12).

Peptides were deposited on ZnSe prism to form a film that is macroscopically thick (see Materials and Methods) and ATR-IR spectra were acquired. These measurements provide information on the conformation the peptides' tend to assume on a surface by a simple drying process. All three peptides show an adsorption band at 1000-1100 cm$^{-1}$ that is associated with the phosphate groups of the phosphserine amino acids[32,33]. In addition, peptides show nicely the amide I, II and III peaks at ~1630, ~1540 and 1300 cm$^{-1}$ respectively[34]. The spectra show differences in both the amide I and II intensities and width which provide evidences for the differences in their conformations[35]. The three peptides show a peak at 1630 cm$^{-1}$ is indicative of peptides in β-sheet conformation. However, the amide I peak profile of pSer and cpSer that induce the β-pleated structure in the anchoring motif appears similar and both also show the amide I weak split at ~1692 cm$^{-1}$ which constitutes a strong evidence for the antiparallel β-sheet arrangement[34,36-39]. The amide I peak of peptide β-cpSer however shows a pronounced shoulder at ~1645 cm$^1$ that corresponds to helical or random structures indicating that this peptide shows significantly lower propensity compared to the two other peptides, towards β-sheet structure in the dry state. The three spectra show a peak at ~1400 cm$^1$ that corresponds to the carboxylate (COO—) symmetric stretching modes in pSer however this peak appears slightly stronger possibly due to the contribution of the Glu-tail motif. All three peptides show the amide II band at ~1545 cm$^{-1}$. In the pSer spectra this peak appears to partially overlap with absorption at ~1520 cm$^{-1}$ that is characteristic of β-sheet structure[40]. This latter band that points to the abundance of β-sheet conformation within the film, is also present to a weaker extent in cpSer spectra and is almost absent in β-cpSer in accordance with the design of these peptide sequences. The relatively strong amide II band at ~1520 in pSer suggests that in the macroscopic film the Glu-tail motif is also packed in β-sheet structure. The differences in peptides conformation detected in the macroscopic film generated on the solid support highlight the strong tendency of pSer and cpSer to assume the β-pleated structure.

Adsorption to Titanium Oxide Micron Size Particles:

Peptide adsorption and desorption conditions were characterized by HPLC. A column was packed with micrometer size particles of the TiO$_2$ anatase phase (see Materials and Methods). Tris buffer saline (TBS), pH 7.4, served as a loading buffer. At this pH the oxide surface is negatively charged[41] hence ruling out the possibility of peptide adsorbing to the interface by electrostatic interactions. The salt ions expected to have an electrostatic repulsion screening effect and make negatively charge TiO$_2$ surface more accessible for the negatively charged peptides to generate coordinative bonds that require short range interaction distance[42]. The elutions used conditions were consecutive linear gradients of sodium bicarbonate (0-200 mM, pH7.4) and NaOH (0-0.1M). The bicarbonate ions may bind by coordinative bonds to the oxide surface, similar to the way phosphate ions can be bound to the surface. Yet the binding strength of the bicarbonate ions to TiO$_2$ is weaker than that of phosphate ions[43]. The chromatograms of all peptides carried with sodium bicarbonate (BC) elution followed by the NaOH gradient (FIGS. 14A-B) showed a main peak during the NaOH gradient, at 85-95 mM. It was previously shown by the present inventors that carboxylic residues doesn't adsorb to $TiO_2$ under these conditions, therefore these results strongly suggest that all peptides become adsorbed by coordinative bonds to the surface through the phosphates groups of the phosphoserine. The tailing peaks shape of pSer and β-cpSer together with the small eluted volume during the void volume of the column probably indicates on impurity of the peptides' powders or secondary interactions of the peptides with the column. Those secondary interactions may occur as a result of different orientation of the phosphate groups at the $TiO_2$ binding surface. The minor differences at the elution times between the peptides shows that this method isn't sensitive enough to provide the information about the affinity of each peptide to $TiO_2$. Therefore, adsorption isotherm to micro-size titanium oxide particles was performed in order to characterize the extent of interactions between the peptides and the oxide (FIGS. 15A-C). The data was fitted to Sips equation (eq.1). Sips isotherms is a combined form of Langmuir and Freundlich expressions and it relies on the assumption that there are a distribution of binding energies of the sites of a surface, this distribution is represented by α. When α→1 Sips equation reduces to Langmuir equation and represents binding of a monolayer with homogenous binding energy and small α values together with low concentrations reduces Sips equation to Freundlich equation with a potential to saturation at high concentrations (unlike the original Freundlich equation). Therefore, fitting peptides adsorption isotherm data to Sips equation give us an insight into their binding energy distributions. Fitting the collected data to Sips equation (continuous line at FIGS. 15A-C and Table 5 herein below) yields α=0.8 for pSer peptide and α=0.4 for control peptides, cpSer and β-cpSer. Table 5 contains the Sips equation values for the three peptides and the standard deviation values (SD).

The high α value for pSer indicated that its adsorption resemble to Langmuir isotherm behavior, monolayer adsorption. However, α value for cpSer and β-cpSer indicate a wider distribution of binding energies, resemble Freundlich isotherm behavior. Two additional values are obtained from the fitting, the maximum amount of molecules adsorbed to $TiO_2$ surface ($S_{max}$) and the association coefficient (k). $S_{max}$ values gives information about the nominal area these peptides occupy at the oxide surface. The $S_{max}$ values for pSer and cpSer are similar (3.33±0.03)·$10^{-7}$ mol $m^{-2}$ and (3.93±0.52)·$10^{-7}$ mol $m^{-2}$, respectively. The inverse of those values provides the nominal area each peptide occupies, the result shows that pSer and cpSer occupy similar area, ~498 $Å^2$ $molec^{-1}$ and ~422 $Å^2$ $molec^{-1}$, respectively. Overall, this result is strong evidence that pSer peptide adsorbing onto $TiO_2$ only through the binding motif and the Glu tail is free. The freedom of movement of the unbounded Glu tail may be the reason for pSer adsorption isotherm is resemble Langmuir monolayer adsorption. However, this value for β-cpSer is calculated to be ~221 $Å^2$ $molec^{-1}$, twice smaller than the other peptides. The reason for that variance can be due to the different sequence of the binding motif, 'pSer-Phe-pSer-Trp' for pSer and cpSer versus 'pSer-pSer-Phe-Trp' for β-cpSer, therefore it can occupy smaller area, also can be seen at the illustration at FIG. 11. The k values represent the affinity between peptides and $TiO_2$, again, pSer and cpSer show resemblance in their results, (21.06±0.60)·$10^3$ $M^{-1}$ and (21.23±14.49)·$10^3 M^{-1}$, respectively. However, the k value for β-cpSer is significantly lower, (3.76±2.15)·$10^3$ $M^{-1}$, this result indicates that β-sheet structured binding motif has stronger binding affinity to $TiO_2$.

TABLE 5

|  | pSer | cpSer | β-cpSer |
|---|---|---|---|
| $R^2$ | 1 | 0.99793 | 0.99953 |
| $S_{max}$ [mol · $m^{-2}$] | 3.33E−7 | 3.93E−7 | 7.48E−7 |
| SD | 3.23E−9 | 5.24E−8 | 0.18E−8 |
| K [$M^{-1}$] | 21.06E3 | 21.29E3 | 3.76E3 |
| SD | 0.60E3 | 14.49E3 | 2.15E3 |
| A | 0.79 | 0.41 | 0.42 |
| SD | 0.01 | 0.04 | 0.02 |

Adsorption to Titanium Oxide Surfaces

Titanium surfaces were prepared by thermal evaporation coating of silicon wafers with 40 nm of pure titanium (see Materials and Methods) and characterized using X-ray photoelectron spectroscopy (XPS). XPS is a surface sensitive technique that detects presence of trace amount of elements on the surface. XPS measurements were performed on the $TiO_2$ surfaces in order to ensure that the oxidation phase is $TiO_2$, a high resolution Ti2p spectrum identified three major peaks (FIG. 16). Two of them refer to the state of titanium in the oxide; a peak at 458.3 eV was attributed to $Ti^{4+}$ $2p_{3/2}$ and a peak at 464 eV to $Ti^{4+}$ $2p_{1/2}$. These peak positions consistent with those observed for $TiO_2$ reference spectra[44,45]. The third peak at 453.5 eV was attributed to $Ti^0$ $2p_{3/2}$ and refers to the state of titanium in the metal; the percentage of this peak was less than 2% therefore a major area of the surface was in oxide state.

Peptide adsorption to $TiO_2$ surfaces was detected using XPS, FIG. 17A shows the atomic concentration of phosphorous (the only source for it is from the phosphoserine amino acids) to that of titanium obtained by survey scans of peptide coated $TiO_2$ surfaces. The results show a similar peptide adsorption for all three peptides. This result is consistent with the adsorption isotherm found for pSer and cpSer peptides. However it contradicts the β-cpSer adsorption isotherm result. This phenomenon can be explained by the different surface topography and surface area between $TiO_2$ particles and $TiO_2$ surface, adsorption surface area at adsorption isotherm experiment is 1.123 $m^2$ and the surface area is $10^{-4}$ $m^2$. At small surface areas, the difference between peptides' adsorption cannot be observed. In order to examine the influence of the Glu tail on calcified mineralization process, titanium oxide surfaces were coated with pSer peptide or with the control peptides (cpSer or β-cpSer) and incubated for 24 hours inside calcium-phosphate solution (see Materials and Methods). Atomic concentrations of calcium and phosphorus were compared with titanium as measured by XPS. The results in FIG. 17B shows that surfaces which were coated with pSer peptide adsorbed significantly higher calcium and phosphate concentration compared to surfaces that were coated with cpSer or β-cpSer peptides. It can be seen that both of the control peptides adsorbed approximately the same calcium and phosphate concentrations due to the fact that both of them are lacking the Glu tail.

Using HPLC with $TiO_2$ microparticles column as described herein, it was also found that Trp-Glu (0.4 mg/ml) in TBS (10 mM, pH=7.4) loading buffer does not adsorb to the oxide. Several solutions of sodium phenyl phosphate dibasic with different concentrations, dissolved in the same TBS, were allowed to adsorb to $TiO_2$ microparticles (1.8 mg/ml in 1 ml). Table 6, herein below lists the initial concentrations and the difference in concentration of the solution between the initial and the one following adsorption. According to Table 6, the phenyl phosphate adsorbs only at concentrations lower than 0.25 mg/ml probably because at higher concentrations the compound undergoes some aggregation and stays only in the solution. This adsorption behavior is unusual and therefore no binding affinity constants were determined.

TABLE 6

| | mg/ml in adsorbing solution | | | | |
|---|---|---|---|---|---|
| | 1 | 0.5 | 0.25 | 0.125 | 0.0625 |
| Difference in concentration of the solution between the initial and the final one. | ~0 | ~0 | 0.008776 | 0.02083 | 0.023648 |

CONCLUSION

The three peptides were found to adsorb coordinatively to $TiO_2$ microparticles as evident by the high pH (~12.6) desorption conditions needed in the HPLC chromatograms to elute the peptides. Differences in peptide's affinity to the $TiO_2$ could not be determined based on the HPLC since the present inventors could not find an elution profile that would widen the range in which the peptides desorb, so to be able to detect with confidence these differences. Therefore adsorption isotherms were performed for each of the peptides. Robust differences were found between the peptides showing that the b-sheet binding motif exhibits higher binding constants compared to the random structure peptide. Based on similar area per molecule occupied by pSer and cpSer it can be deduced that pSer is bound to the surface through the binding motif while its tail is pointing away from the surface. This result is also supported by the XPS measurements in which it was found that pSer adsorbs more Ca and P ions compared to the two other control peptides.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating or repairing a tissue, the method comprising implanting an article of manufacture selected from the group consisting of a dental impant, a hip prosthesis, a knee prosthesis, a heart valve, and an intravascular stent comprising a titanium surface and an isolated peptide adsorbed to said surface into a subject in need thereof, said isolated peptide comprising a titanium oxide binding amino acid sequence connected to a heterologous biologically active amino acid sequence via a beta sheet breaker linker, wherein:

(i) said titanium oxide binding amino acid sequence is selected to bind coordinatively with titanium oxide;

(ii) said titanium oxide binding amino acid sequence is selected to induce a beta sheet structure;
(iii) said titanium oxide binding amino acid sequence binds to titanium oxide with a higher affinity than said biologically active amino acid sequence binds to said titanium oxide under physiological conditions; and
(iv) said titanium oxide binding amino acid sequence comprises the sequence Z-X-Z-X, wherein X is any hydrophobic amino acid and Z is phosphoserine or L-DOPA, thereby generating or repairing the tissue.

2. The method of claim 1, wherein said tissue is selected from the group consisting of bone, cartilage and cardiac tissue.

3. The method of claim 1, wherein said titanium oxide binding amino acid sequence binds to titanium oxide with at least 2 fold higher affinity than said biologically active amino acid sequence.

4. The method of claim 1, wherein said beta sheet breaker amino linker comprises 2-7 repeating glycine residues.

5. The method of claim 4, wherein said beta sheet breaker amino acid linker is set forth by Gly-Gly-Gly.

6. The method of claim 1, wherein said titanium oxide binding amino acid sequence comprises no more than 7 carboxyl amino acid residues.

7. The method of claim 1, wherein said titanium oxide binding amino acid sequence comprises alternating hydrophilic, negatively charged amino acids and hydrophobic amino acids.

8. The method of claim 7, wherein said alternating hydrophilic and hydrophobic amino acid sequence is not repeated more than 7 times.

9. The method of claim 1, wherein at least one of the amino acids of said titanium oxide binding amino acid sequence is phosphorylated.

10. The method of claim 1, wherein said titanium oxide binding amino acid sequence comprises the sequence selected from the group consisting of pSer-X-pSer-X (SEQ ID NO: 6), wherein X is any hydrophobic amino acid.

11. The method of claim 1, comprising the sequence as set forth in Z-X-Z-X-(Gly)$_3$-(Y)$_5$ (SEQ ID NO: 9) where Z is L-dopa or phosphoserine, where X is any hydrophobic amino acid and Y is aspartic acid or glutamic acid.

12. The method of claim 1, wherein said peptide comprises the sequence selected from the group consisting of SEQ ID NO: 1, SEQ ID NO: 2, SEQ ID NO: 4 and SEQ ID NO: 12.

13. The method of claim 1, wherein when said titanium oxide binding amino acid sequence comprises the sequence Pro-pSer-X-pSer-X (SEQ ID NO: 6), where X is a hydrophobic amino acid, said biologically active amino acid sequence is SEQ ID NO: 7.

14. The method of claim 1, wherein when said titanium oxide binding amino acid sequence comprises the sequence L-DOPA-X-L-DOPA-X (SEQ ID NO: 5), where X is a hydrophobic amino acid, said biologically active amino acid sequence is SEQ ID NO: 7.

15. The method of claim 1, wherein said titanium oxide binding amino acid sequence comprises the sequence PSer-Phe.

* * * * *